United States Patent [19]

Maw et al.

[11] Patent Number: 5,767,139
[45] Date of Patent: Jun. 16, 1998

[54] INDOLES WHICH HAVE STEROID 5-α REDUCTASE INHIBITORY ACTIVITY

[75] Inventors: Graham Nigel Maw; Julian Blagg; Colin William Greengrass; Paul William Finn, all of Sandwich, United Kingdom

[73] Assignee: Pfizer, Inc., New York, N.Y.

[21] Appl. No.: 256,734

[22] PCT Filed: Feb. 16, 1993

[86] PCT No.: PCT/EP93/00380

§ 371 Date: Aug. 2, 1994

§ 102(e) Date: Aug. 2, 1994

[87] PCT Pub. No.: WO93/17014

PCT Pub. Date: Sep. 2, 1993

[30] Foreign Application Priority Data

Feb. 28, 1992 [GB] United Kingdom ............ 9204365

[51] Int. Cl.$^6$ .................... A01N 43/38; A61K 31/41
[52] U.S. Cl. ................ 514/38; 514/382; 514/414; 514/418; 514/419; 548/253; 548/452; 548/454; 548/492; 548/493
[58] Field of Search ............... 548/452, 492, 548/493, 454, 253; 514/414, 418, 419, 381, 382

[56] References Cited

U.S. PATENT DOCUMENTS 5,696,146  12/1997  Blagg et al. ................ 514/414

*Primary Examiner*—Johann Richter
*Assistant Examiner*—Taofiq A. Solola
*Attorney, Agent, or Firm*—Peter C. Richardson; Paul H. Ginsburg; Grover F. Fuller, Jr.

[57] ABSTRACT

The present invention provides compounds of the formula:

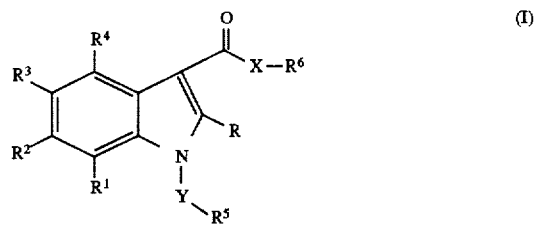

and the pharmaceutically acceptable salts thereof, together with pharmaceutically compositions containing, uses of, processes for the preparation of and intermediates used in the preparation of, such compounds.

14 Claims, No Drawings

INDOLES WHICH HAVE STEROID 5-α REDUCTASE INHIBITORY ACTIVITY

This application is a 371 of PCT EP93/00380 filed Feb. 16, 1993

This invention relates to indole derivatives which have steroid 5α-reductase inhibitory activity.

More particularly this invention relates to indoles, their preparation and their use as testosterone-5α-reductase inhibitors.

The androgen class of steroidal hormones is responsible for the difference in the physical characteristics of males and females. Of all the organs that produce androgens, the testes produce these hormones in the greatest amounts. Overproduction of these hormones in the body results in many undesirable physical manifestations and disease states, e.g. acne vulgaris, alopecia, seborrhoea, female hirsutism, benign prostatic hypertrophy and male pattern baldness.

The principal androgen secreted by the testes is testosterone and it is the primary androgen present in male plasma. The principal mediator of androgenic activity in certain organs such as the prostate and sebaceous gland are the 5α-reduced androgens. Testosterone is therefore the prohormone of 5α-dihydrotestosterone which is formed locally in the above organs by the action of testosterone-5α-reductase. The presence of elevated levels of dihydrotestosterone in many disease states has therefore focussed attention on the synthesis of testosterone 5α-reductase inhibitors.

Testosterone 5α-reductase inhibitors may also be useful in the treatment of human prostate adenocarcinomas.

EP-A-0458207 discloses indole derivatives with testosterone 5α-reductase inhibitory activity.

The present invention provides compounds of the formula:

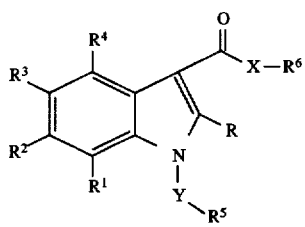
(I)

and pharmaceutically acceptable salts thereof,
wherein
X is O, NH, N($C_1$–$C_4$ alkyl), direct link, $C_1$–$C_4$ alkylene, $C_2$–$C_4$ alkenylene or $C_2$–$C_4$ alkynylene, said alkylene, alkenylene and alkynylene being optionally substituted by $C_1$–$C_4$ alkyl or aryl;

Y is methylene, $C_2$–$C_6$ alkylene optionally interrupted by O, $C_2$–$C_6$ alkenylene or $C_2$–$C_6$ alkynylene, all of which may be optionally substituted by $C_1$–$C_6$ alkyl, or is a group of the formula:

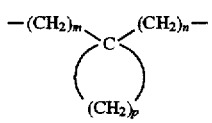

wherein m and n are each independently selected from 0 and an integer of from 1 to 5, with the proviso that the sum of m and n is not greater than 5, and p is an integer of from 2 to 6;

R is H, OH, halo, $C_1$–$C_4$ alkyl or $C_1$–$C_4$ alkoxy;
$R^1$, $R^2$, $R^3$ and $R^4$ are each independently selected from H, $C_1$–$C_4$ alkyl, $C_1$–$C_4$ alkoxy, OH, halo, —$CF_3$, —$CO_2$($C_1$–$C_4$ alkyl), —$CONH_2$, —$CONH(C_1$–$C_4$ alkyl) and —$CON(C_1$–$C_4$ alkyl)$_2$;
$R^5$ is —COOH, —$COOR^7$, —$CONR^8R^9$ or tetrazol-5-yl;
$R^6$ is

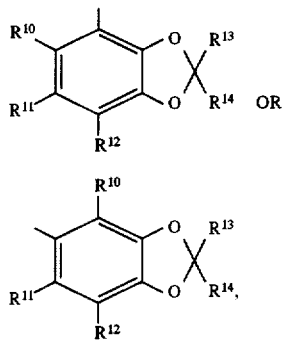

$R^7$ is a biolabile ester-forming group;
$R^8$ and $R^9$ are each independently selected from H and $C_1$–$C_4$ alkyl;
$R^{10}$, $R^{11}$ and $R^{12}$ are each independently selected from H, $C_1$–$C_4$ alkyl, $C_1$–$C_4$ alkoxy, —OH, halo and halo($C_1$–$C_4$ alkyl);
$R^{13}$ and $R^{14}$ are each independently selected from H, $C_1$–$C_{10}$ alkyl, $C_1$–$C_{10}$ alkoxy, $C_2$–$C_6$ alkenyl, $C_2$–$C_6$ alkynyl, $C_3$–$C_8$ cycloalkyl, —$CO_2$($C_1$–$C_4$ alkyl), —$CONR^8R^9$, —CN, halo($C_1$–$C_6$ alkyl), aryl and heteroaryl, said alkyl and alkoxy groups being optionally substituted by $C_1$–$C_6$ alkoxy, $C_3$–$C_7$ cycloalkyl, —OH, —$CO_2$($C_1$–$C_4$ alkyl), —$CONR^8R^9$, —CN, aryl, aryloxy or heteroaryl, and said alkenyl and alkynyl groups being optionally substituted by aryl, with the proviso that $R^{13}$ and $R^{14}$ are not both H, or $R^{13}$ and $R^{14}$, taken together with the carbon atom to which they are attached, represent optionally benzo-fused spiro($C_3$–$C_8$)cycloalkane, said spirocycloalkane group and the benzo-fused portion being optionally substituted by $C_1$–$C_6$ alkyl, $C_1$–$C_6$alkoxy, $C_3$–$C_8$ cycloalkyl, —OH, —$CO_2$($C_1$–$C_4$ alkyl), —$CONR^8R^9$, —CN, halo($C_1$–$C_6$ alkyl), aryl or heteroaryl, or $R^{13}$ and $R^{14}$, taken together with the carbon atom to which they are attached, represent spiropyrrolidine or spiropiperidine, both of which may be optionally N-substituted by $C_1$–$C_6$ alkyl, $C_2$–$C_6$ alkanoyl, $C_2$–$C_6$ alkanoyl($C_1$–$C_4$ alkyl)- or arylcarbonyl;

"aryl" used in the definitions of X, $R^{13}$ and $R^{14}$ means phenyl optionally substituted by $C_1$–$C_6$ alkyl, $C_1$–$C_6$ alkoxy, $C_2$–$C_6$ alkenyl, OH, halo, halo($C_1$–$C_6$ alkyl), nitro, amino, $C_2$–$C_6$ alkanamido, $C_2$–$C_6$ alkanoyl, —$CO_2$ ($C_1$–$C_4$ alkyl), phenyl, phenyl($C_1$–$C_4$)alkoxy or —($CH_2$)$_q$$CONR^8R^9$ wherein q is 0 or an integer of from 1 to 4; and "heteroaryl" used in the definitions of $R^{13}$ and $R^{14}$ means a five- or six-membered heteroaromatic group which contains from 1 to 4 heteroatoms each independently selected from N, O and S and which is optionally substituted by $C_1$–$C_4$ alkyl, $C_1$–$C_4$ alkoxy, halo, —OH or halo-($C_1$–$C_4$ alkyl).

Alkyl and alkoxy groups containing three or more carbon atoms and alkenyl, alkanamido and alkanoyl groups containing four or more carbon atoms may be straight- or branched-chain.

The term "halo" means fluoro, chloro, bromo or iodo.

The term "biolabile ester-forming group" is well understood in medicinal chemistry as meaning a group which forms an ester which can be readily cleaved in vivo to liberate the corresponding acid of the formula (I) wherein $R^5$ is —COOH. A number of such ester groups are well-known, for example in the penicillin area or in the case of the angiotensin-converting enzyme (ACE) inhibitor antihypertensive agents.

Esters of the formula (I) wherein $R^5$ is —$COOR^7$ wherein $R^7$ is $C_1$–$C_6$ alkyl are steroid 5α-reductase inhibitors per se but, in general, esters where $R^7$ is a biolabile ester-forming group are useful as pro-drugs to provide compounds of the formula (I) wherein $R^5$ is —COOH in vivo following oral administration. Such esters are also useful as intermediates for the preparation of compounds of the formula (I) wherein $R^5$ is —COOH.

The suitability of any particular ester-forming group for this purpose can be assessed by conventional in vitro or in vivo enzyme hydrolysis studies.

Examples of biolabile ester-forming groups are alkyl, alkanoyloxyalkyl (including alkyl, cycloalkyl or aryl substituted derivatives thereof), arylcarbonyl-oxyalkyl (including aryl substituted derivatives thereof), aryl, arylalkyl, indanyl and haloalkyl: wherein alkanoyl groups have from 2 to 8 carbon atoms, alkyl groups have from 1 to 8 carbon atoms and aryl means phenyl or naphthyl, both of which may be optionally substituted by $C_1$–$C_4$ alkyl, $C_1$–$C_4$ alkoxy or halo. Alkyl, alkanoyl and alkoxy groups can, where appropriate, be straight- or branched-chain.

Specific examples of biolabile ester-forming groups are $C_1$–$C_6$ alkyl (e.g. methyl, ethyl, n-propyl, isopropyl), benzyl, 1-(2,2-diethylbutyryloxy)ethyl, 2-ethylpropionyloxymethyl, 1-(2-ethylpropionyloxy)ethyl, 1-(2,4-dimethylbenzoyloxy)ethyl, α-benzoyloxybenzyl, 1-(benzoyloxy)ethyl, 2-methyl-1-propionyloxy-1-propyl, 2,4,6-trimethylbenzoyloxymethyl, 1-(2,4,6-trimethylbenzoyloxy)ethyl, pivaloyloxymethyl, phenethyl, phenpropyl, 2,2,2-trifluoroethyl, 1- or 2-naphthyl, 2,4-dimethylphenyl, 4-t-butylphenyl and 5-indanyl.

The pharmaceutically acceptable salts of the compounds of the formula (I) include suitable acid addition and base salts thereof.

Suitable acid addition salts are formed from acids which form non-toxic salts and examples thereof are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and p-toluenesulphonate salts.

Suitable base salts are formed from bases which form non-toxic salts and examples thereof are the aluminium, calcium, lithium, magnesium, potassium, sodium, zinc, N-benzyl-N-(2-phenylethyl)amine, 1-adamantylamine and diethanolamine salts.

Preferred base salts are the sodium, potassium, N-benzyl-N-(2-phenylethyl)amine and 1-adamantylamine salts.

For a review on suitable pharmaceutical salts see Berge et al, J. Pharm. Sci., 66, 1–19 (1977).

In a preferred aspect of the present invention "aryl" means phenyl optionally substituted by up to 3 substituents and preferably means phenyl optionally substituted by 1 or 2 substituents.

In a further preferred aspect of the present invention "heteroaryl" means pyrrolyl, furyl, thienyl, imidazolyl, thiazolyl, triazolyl, pyridinyl, pyrimidinyl, pyridazinyl or pyrazinyl, all of which may be optionally substituted by $C_1$–$C_4$ alkyl, $C_1$–$C_4$ alkoxy, halo, —OH or halo($C_1$–$C_4$ alkyl).

In the above definitions relating to the present invention:
Preferably X is direct link or $C_1$–$C_4$ alkylene. More preferably X is direct link or methylene. Most preferably X is direct link.

Preferably Y is $C_1$–$C_6$ alkylene. More preferably Y is ethylene, propylene or butylene. Most preferably Y is propylene.

Preferably R is H or $C_1$–$C_4$ alkyl. More preferably R is H or methyl. Most preferably R is H.

Preferably $R^1$, $R^2$, $R^3$ and $R^4$ are each H.

Preferably $R^5$ is —COOH or —$COOR^7$ where $R^7$ is as defined for a compound of the formula (I). More preferably $R^5$ is —COOH or —COO($C_1$–$C_6$ alkyl). Yet more preferably $R^5$ is —COOH or —$COOC_2H_5$. Most preferably $R^5$ is —COOH.

Preferably $R^6$ is

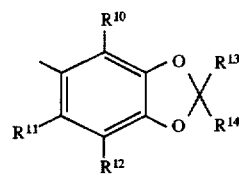

wherein $R_{10}$ to $R^{14}$ are as previously defined for a compound of the formula (I).

Preferably $R^{10}$, $R^{11}$ and $R^{12}$ are each H.

Preferably $R^{13}$ and $R^{14}$ are each independently selected from H, $C_1$–$C_{10}$ alkyl optionally substituted by $C_1$–$C_6$ alkoxy, $C_2$–$C_6$ alkynyl, $C_3$–$C_8$ cycloalkyl, aryl and heteroaryl, with the proviso that $R^{13}$ and $R^{14}$ are not both H, or $R^{13}$ and $R^{14}$, taken together with the carbon atom to which they are attached, represent optionally benzo-fused spiro ($C_3$–$C_8$)cycloalkane, optionally substituted by —CN or aryl. More preferably $R^{13}$ and $R^{14}$ are each independently selected from H, $C_1$–$C_{10}$ alkyl optionally substituted by $C_1$–$C_6$ alkoxy, $C_2$–$C_6$ alkynyl, $C_3$–$C_8$ cycloalkyl, phenyl optionally substituted by $C_1$–$C_6$ alkyl, $C_1$–$C_6$ alkoxy, halo, halo($C_1$–$C_6$ alkyl) or phenyl($C_1$–$C_4$)alkoxy, thienyl and furyl, with the proviso that $R^{13}$ and $R^{14}$ are not both H, or $R^{13}$ and $R^{14}$, taken together with the carbon atom to which they are attached, represent optionally benzo-fused spiro($C_5$–$C_7$) cycloalkane, optionally substituted by —CN or phenyl. Yet more preferably $R^{13}$ and $R^{14}$ are each independently selected from H, methyl, ethyl, n-propyl, n-butyl, t-butyl, 3-methoxyprop-1-yl, 1-propynyl, cyclohexyl, phenyl, 4-methylphenyl, 4-ethylphenyl, 4-(n-propyl)phenyl, 4-(2-methylpropyl)phenyl, 3,4-dimethylphenyl, 4-fluorophenyl, 2-chlorophenyl, 4-chlorophenyl, 3,4-dichlorophenyl, 4-methoxyphenyl, 4-trifluoromethylphenyl, 4-benzyloxyphenyl, cyclohexyl, 2-thienyl and 2-furyl, with the proviso that $R^{13}$ and $R^{14}$ are not both H, or $R^{13}$ and $R^{14}$, taken together with the carbon atom to which they are attached, represent spirocyclohexane, spirocycloheptane, or a group of the formula:

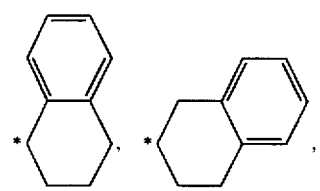

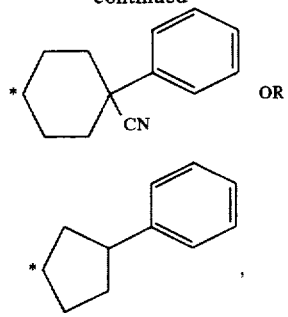

where * represents the Spiro carbon atom in common with the 1,3-benzodioxolane ring. Most preferably either $R^{13}$ and $R^{14}$ are both phenyl or $R^{13}$ is methyl and $R^{14}$ is 4-(2-methylpropyl)phenyl.

A compound of the formula (I) may contain one or more asymmetric carbon atoms and/or one or more non-aromatic carbonp13 carbon double bonds and may therefore exist in two or more stereoisomeric forms. The present invention includes both the individual stereoisomers of the compounds of the formula (I) together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of a racemate using a suitable chiral support or by fractional crystallisation of the diastereoisomeric salts formed by reaction of a racemate with a suitable optically active acid or base.

Preferred compounds of the formula (I) are 4-[3-([2-methyl-2-(4-[2-methylpropyl]phenyl)-1,3-benzodioxolan-5-yl]carbonyl)indol-1-yl]butanoic acid and ethyl 4-[3-([2-methyl-2-(4-[2-methylpropyl]phenyl)-1,3-benzodioxolan-5-yl]carbonyl)indol-1-yl]butanoate and the pharmaceutically acceptable salts thereof.

Particularly preferred compounds of the formula (I) are (-)-4-[3-([2-methyl-2-(4-[2-methylpropyl]phenyl)-1,3-benzodioxolan-5-yl]carbonyl)indol-1-yl]butanoic acid and (-)-ethyl 4-[3-([2-methyl-2-(4-[2-methylpropyl]phenyl)-1,3-benzodioxolan-5-yl)carbonyl)indol-1-yl]butanoate and the pharmaceutically acceptable salts thereof.

Preferred intermediates used in the preparation of the above preferred compounds of the formula (I) are 2-methyl-2-[4-(2-methylpropyl)phenyl]-1,3-benzodioxolane-5-carboxylic acid, (-)-2-methyl-2-(4-(2-methylpropyl)-phenyl]-1,3-benzodioxolane-5-carboxylic acid and the (-)-α-methylbenzylamine salt thereof, 3-([2-methyl-2-(4-[2-methylpropyl]phenyl)-1,3-benzodioxolan-5-yl]carbonyl) indole and (-)-3-([2-methyl-2-(4-[2-methylpropyl]phenyl)-1,3-benzodioxolan-5-yl]carbonyl)indole.

The compounds of formula (I) provided by the invention may be prepared by the following methods:

1) The compounds of the formula (I) wherein $R^5$ is —COOH and X, Y, R, $R^1$ to $R^4$ and $R^6$ are as previously defined for a compound of the formula (I) may be prepared by cleavage of an ester of the formula:

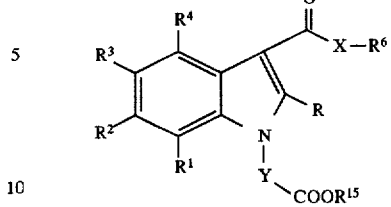

(II)

wherein $R^{15}$ is a suitable ester-forming group and X, Y, R, $R^1$ to $R^4$ and $R^6$ are as previously defined for a compound of the formula (I).

A plethora of suitable ester-forming groups that may be cleaved to provide the corresponding carboxylic acid are known to the skilled man, see, e.g., T. W. Greene, "Protective Groups in Organic Synthesis", Wiley-Interscience (1981).

Where $R^{15}$ is an ester-forming group that may be removed by hydrolysis, e.g. a biolabile ester-forming group as previously defined such as $C_1$–$C_6$ alkyl (i.e. a compound of the formula (I) wherein $R^5$ is —COOR$^7$), the hydrolysis may be carried out under acidic or basic conditions, e.g. using an aqueous solution of either a suitable mineral acid or a suitable inorganic base. Preferably the hydrolysis is carried out under basic conditions.

In a typical procedure an ester of the formula (II) is treated with an aqueous solution of a suitable base, e.g. sodium or potassium hydroxide, and in the presence of a suitable organic co-solvent, e.g. tetrahydrofuran or a $C_1$–$C_4$ alkanol (e.g. methanol or ethanol) or a combination thereof. The hydrolysis is typically carried out at from room temperature to the reflux temperature. The product is obtained as a base salt which may be converted to the carboxylic acid by acidification in the work-up procedure.

Where $R^{15}$ is an ester-forming group that may be removed by reduction, e.g. benzyl, the reduction may be carried out by catalytic hydrogenation using, e.g., palladium-on-charcoal, as the catalyst.

2) The compounds of the formula (I) wherein $R^5$ is —COOH and X, Y, R, $R^1$ to $R^4$ and $R^6$ are as previously defined for a compound of the formula (I) may be prepared by hydrolysis of a compound of the formula (I) wherein $R^5$ is —CONR$^8$R$^9$ wherein X, Y, R, $R^1$ to $R^4$, $R^6$, $R^8$ and $R^9$ are as previously defined for a compound of the formula (I).

The hydrolysis may be carried out under acidic or basic conditions, e.g. using an aqueous solution of either a suitable mineral acid, e.g. hydrochloric or sulphuric acid, or a suitable inorganic base, e.g. sodium or potassium hydroxide, at from room temperature to the reflux temperature. When basic hydrolysis conditions are used the product is obtained as a base salt which may be converted to the carboxylic acid by acidification in the work-up procedure.

3) The compounds of the formula (I) wherein $R^5$ is —COOH and X, Y, R, $R^1$ to $R^4$ and $R^6$ are as previously defined for a compound of the formula (I) may be prepared by hydrolysis of a compound of the formula:

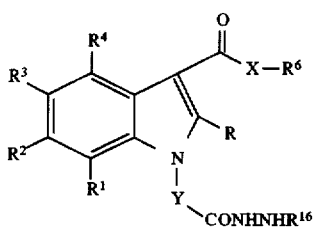

wherein X, Y, R, $R^1$ to $R^4$ and $R^6$ are as previously defined for a compound of the formula (I) and $R^{16}$ is H or $C_1$–$C_4$ alkyl.

The hydrolysis may be carried out under acidic or basic conditions, e.g. using an aqueous solution of either a suitable acid, e.g. hydrochloric or acetic acid, or a suitable inorganic base, e.g. sodium or potassium hydroxide, at from room temperature to the reflux temperature. When basic hydrolysis conditions are used the product is obtained as a base salt which may be converted to the carboxylic acid by acidification in the work-up procedure.

4) The compounds of the formula (I) wherein $R^5$ is —COOH and X, Y, R, $R^1$ to $R^4$ and $R^6$ are as previously defined for a compound of the formula (I) may be prepared by hydrolysis of a compound of the formula:

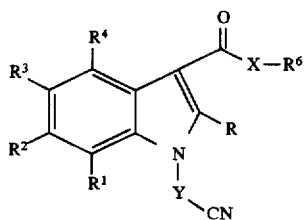

wherein X, Y, R, $R^1$ to $R^4$ and $R^6$ are as previously defined for a compound of the formula (I).

The hydrolysis may be carried out under acidic or basic conditions, e.g. using an aqueous solution of either a suitable acid, e.g. hydrochloric or sulphuric acid, or a suitable inorganic base, e.g. sodium or potassium hydroxide, at from room temperature to the reflux temperature. When basic conditions are used hydrogen peroxide may optionally be present and also the product is obtained as a base salt which may be converted to the carboxylic acid by acidification in the work-up procedure.

5) The compounds of the formula (I) wherein $R^5$ is —COOH and X, Y, R, $R^1$ to $R^4$ and $R^6$ are as previously defined for a compound of the formula (I) may be prepared by acidic hydrolysis of a compound of the formula:

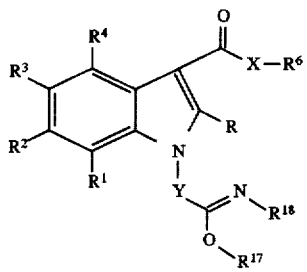

wherein X, Y, R, $R^1$ to $R^4$ and $R^6$ are as previously defined for a compound of the formula (I) and $R^{17}$ and $R^{18}$ taken together represent ethylene, said ethylene being optionally substituted by phenyl or $C_1$–$C_4$ alkyl (preferably methyl). Preferably $R^{17}$ and $R^{18}$ taken together represent —$CH_2C(CH_3)_2$—.

The hydrolysis may be carried out using an aqueous solution of a suitable acid such as hydrochloric acid at from room temperature to the reflux temperature.

6) The compounds of the formula (I) wherein $R^5$ is —$CONH_2$ and X, Y, R, $R^1$ to $R^4$ and $R^6$ are as previously defined for a compound of the formula (I) may be prepared by partial hydrolysis of a compound of the formula (IV) wherein X, Y, R, $R^1$ to $R^4$ and $R^6$ are as previously defined for a compound of the formula (I). The hydrolysis may be carried out using concentrated sulphuric acid at from 0° C. to room temperature.

7) The compounds of the formula (I) wherein $R^5$ is —$COOR^7$ wherein X, Y, R, $R^1$ to $R^4$, $R^6$ and $R^7$ are as previously defined for a compound of the formula (I) may be prepared by esterification of a compound of the formula (I) wherein $R^5$ is —COOH and X, Y, R, $R^1$ to $R^4$ and $R^6$ are as previously defined for a compound of the formula (I) with an alcohol of the formula $R^7OH$ wherein $R^7$ is as previously defined for this method.

The reaction may be carried out under classical esterification conditions such as by using an excess of the alcohol and with acid catalysis, e.g. by sulphuric acid or p-toluenesulphonic acid, at from room temperature to the reflux temperature. The water generated during the reaction may be removed by azeotropic distillation or by the use of a dehydrating agent or a molecular sieve.

The esterification may also be carried out by reacting the acid with the alcohol in the presence of a dehydrating agent, e.g. dicyclohexylcarbodiimide or diethylazodicarboxylate/triphenylphosphine (see O. Mitsunobu, Synthesis, 1981, 1).

Alternatively the esterification may be carried out by first forming an activated ester or imidazolide derivative of the carboxylic acid, followed by reaction of the activated ester or imidazolide in situ with the alcohol of the formula $R^7OH$. An activated ester may be formed by reacting the carboxylic acid with 1-hydroxybenzotriazole in the presence of a suitable dehydrating agent, e.g. 1-(3-N,N-dimethylaminopropyl)-3-ethylcarbodiimide, and in a suitable solvent, e.g. dichloromethane, at room temperature. An imidazolide may be formed by reacting the carboxylic acid with 1,1'-carbonyldiimidazole in a suitable solvent, e.g. dichloromethane, at room temperature.

8) The compounds of the formula (I) wherein $R^5$ is —$COOR^7$ wherein X, Y, R, $R^1$ to $R^4$, $R^6$ and $R^7$ are as previously defined for a compound of the formula (I) may be prepared by reaction of a compound of the formula:

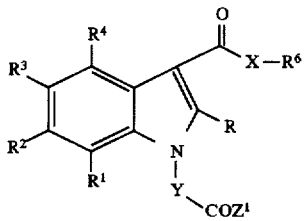

wherein X, Y, R, $R^1$ to $R^4$ and $R^6$ are as previously defined for a compound of the formula (I) and $Z^1$ is a leaving group, e.g. chloro or bromo, with an alcohol of the formula $R^7OH$ wherein $R^7$ is as previously defined for this method.

The reaction may be carried out in the presence of an acid acceptor, e.g. pyridine, and in a suitable solvent, e.g. dichloromethane, at from 0° C. to room temperature.

9) The compounds of the formula (I) wherein $R^5$ is —$COOR^7$ wherein X, Y, R, $R^1$ to $R^4$, $R^6$ and $R^7$ are as previously defined for a compound of the formula (I) may be prepared by reaction of a base salt of a compound of the formula (I) wherein $R^5$ is —COOH and X, Y, R, $R^1$ to $R^4$ and $R^6$ are as previously defined for a compound of the formula (I) (i.e. a carboxylate base salt) with a compound of the formula $R^7Z^2$ wherein $R^7$ is as previously defined for a compound of the formula (I) and $Z^2$ is a suitable leaving group, e.g. halo, preferably bromo or iodo, or p-toluenesulphonyloxy. Preferred base salts of a compound of the formula (I) for use in this method include the sodium and potassium salts. The reaction may be carried out in a suitable solvent, e.g. dimethylformamide or tetrahydrofuran, at from room temperature to the reflux temperature.

10) The compounds of the formula (I) wherein $R^5$ is —CONR$^8$R$^9$ and X, Y, R, $R^1$ to $R^4$, $R^6$, $R^8$ and $R^9$ are as previously defined for a compound of the formula (I) may be prepared by reaction of a compound of the formula (I) wherein $R^5$ is —COOH and X, Y, R, $R^1$ to $R^4$ and $R^6$ are as previously defined for a compound of the formula (I) with an amine of the formula $R^8R^9NH$ wherein $R^8$ and $R^9$ are as previously defined for this method in the presence of a dehydrating agent, e.g. dicyclohexylcarbodiimide. The reaction may be carried out in a suitable organic solvent, e.g. dichloromethane, at from room temperature to the reflux temperature.

Alternatively the reaction may be carried out by first forming an activated ester or imidazolide derivative of the carboxylic acid, followed by reaction of the activated ester or imidazolide in situ with the amine of the formula $R^8R^9NH$. Suitable procedures for the formation of an activated ester or imidazolide are described in method (7)

11) The compounds of the formula (I) wherein $R^{10}$ is —CONR$^8$R$^9$ and X, Y, R, $R^1$ to $R^4$, $R^6$, $R^8$ and $R^9$ are as previously defined for a compound of the formula (I) may be prepared by reaction of a compound of the formula (VI) wherein X, Y, R, $R^1$ to $R^4$, $R^6$ and $Z^1$ are as previously defined for a compound of the formula (VI) with an amine of the formula $R^8R^9NH$ wherein $R^8$ and $R^9$ are as previously defined for this method. The reaction may be carried out in the presence of an acid acceptor, e.g. pyridine, and in a suitable solvent, e.g. dichloromethane, at from 0° C. to room temperature.

12) The compounds of the formula (I) wherein $R^{10}$ is —CONR$^8$R$^9$ and X, Y, R, $R^1$ to $R^4$, $R^6$, $R^8$ and $R^9$ are as previously defined for a compound of the formula (I) may be prepared by reaction of a compound of the formula (II) wherein $R^{15}$ is a suitable ester-forming group, e.g. a biolabile ester-forming group as previously defined such as $C_1$–$C_6$ alkyl (i.e. a compound of the formula (I) wherein $R^5$ is —COOR$^7$), or p-nitrophenyl, and X, Y, R, $R^1$ to $R^4$ and $R^6$ are as previously defined for a compound of the formula (I) with an amine of the formula $R^8R^9NH$ wherein $R^8$ and $R^9$ are as previously defined for this method. The reaction may be carried out in a suitable solvent, e.g. a $C_1$–$C_4$ alkanol, at from room temperature to the reflux temperature. The reaction is usually carried using an excess of the amine and in a sealed reaction vessel.

13) The compounds of the formula (I) wherein $R^5$ is —COOH or —CONR$^8$R$^9$, X is direct link, $C_1$–$C_4$ alkylene, $C_2$–$C_4$ alkenylene or $C_2$–$C_4$ alkynylene, said alkylene, alkenylene and alkynylene being optionally substituted by $C_1$–$C_4$ alkyl or aryl, and Y, R, $R^1$ to $R^4$, $R^6$, $R_8$ and $R^9$ are as previously defined for a compound of the formula (I) may be prepared by acidic hydrolysis of a compound of the formula:

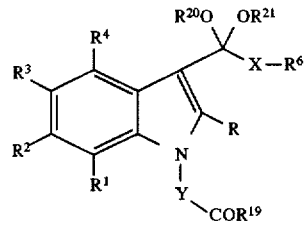

wherein X, Y, R, $R^1$ to $R^4$ and $R^6$ are as previously defined for this method, $R^{20}$ and $R^{21}$ are either each $C_1$–$C_4$ alkyl or when taken together represent $C_2$–$C_3$ alkylene, said alkylene being optionally substituted by $C_1$–$C_4$ alkyl, and $R^{19}$ is —OH, —OR$^{22}$ wherein $R^{22}$ is a suitable ester-forming group that may be removed by hydrolysis, e.g. a biolabile ester-forming group as previously defined such as $C_1$–$C_6$ alkyl, or NR$^8$R$^9$ wherein $R^8$ and $R^9$ are as previously defined for this method, as appropriate. The hydrolysis may be carried out using a suitable acid, e.g. hydrochloric acid or p-toluenesulphonic acid, in the presence of water.

The compounds of the formula (VII) may be prepared by first forming the corresponding ketal of a compound of the formula (VIII) wherein X, R, $R^1$ to $R^4$ and $R^6$ are as previously defined for this method, by reacting with the appropriate alcohol under acidic conditions, e.g. see T. W. Greene, "Protective Groups in Organic Synthesis", Wiley-Interscience (1981), followed by N-alkylation of the ketal by a similar procedure to that described in method (14) for alkylation of a compound of the formula (VIII).

14) All the compounds of the formula (I) wherein X, Y, R and $R^1$ to $R^6$ are as previously defined for a compound of the formula (I) may be prepared by alkylation of a base salt (i.e. the N-deprotonated form) of a compound of the formula:

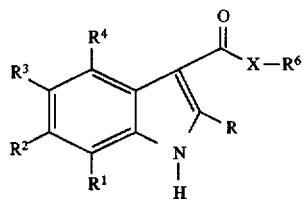

wherein X, R, $R^1$ to $R^4$ and $R^6$ are as previously defined for a compound of the formula (I) with a compound of the formula $Z^3$—Y—COOR$^7$, $Z^3$—Y—CONR$^8$R$^9$ or a base salt of a compound of the formula $Z^3$—Y—COOH wherein Y, $R^7$, $R^8$ and $R^9$ are as previously defined for a compound of the formula (I) and $Z^3$ is a leaving group, e.g. halo, preferably chloro, bromo or iodo, methanesulphonyloxy or p-toluenesulphonyloxy. The preferred base salts of the compounds of the formula $Z^3$—Y—COOH include the alkali metal and alkaline earth metal salts, e.g. the sodium and potassium salts. The preferred base salts of the compounds of the formula (VIII) include the alkali metal salts, e.g. the sodium and potassium salts.

The reaction may be performed by initial deprotonation of a compound of the formula (VIII) with a suitable base, e.g. sodium hydride or potassium carbonate, followed by reaction of the resulting anion with a compound of the formula $Z^3$—Y—COOR$^7$, $Z^3$—Y—CONR$^8$R$^9$ or a base salt of a compound of the formula $Z^3$—Y—COOH, as required. The reaction may be carried out in a suitable solvent, e.g. N,N-dimethylformamide, tetrahydrofuran or 2-butanone, at from 0° C. to the reflux temperature.

Alternatively the reaction may be carried out under phase transfer conditions where a suitable base is sodium or potassium hydroxide.

Where a compound of the formula (I) wherein $R^5$ is —COOH is required the product is obtained as a base salt which may be converted to the carboxylic acid by acidification in the work-up procedure.

15) The compounds of the formula (I) wherein X is direct link, $C_1$–$C_4$ alkylene, $C_2$–$C_4$ alkenylene or $C_2$–$C_4$ alkynylene, said alkylene, alkenylene and alkynylene being optionally substituted by $C_1$–$C_4$ alkyl or aryl, and Y, R and $R^1$ to $R^6$ are as previously defined for a compound of the formula (I) may be prepared by acylation of an indole of the formula:

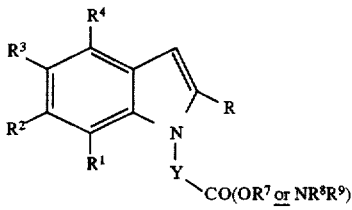

or, where R is OH, a base salt thereof, or of a base salt of an indole of the formula:

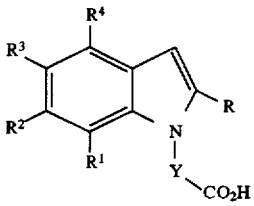

wherein Y, R, $R^1$ to $R^4$, $R^7$ $R^8$ and $R^9$ are as previously defined for a compound of the formula (I), with a compound of the formula:

$$R^6XCOZ^4 \qquad (XI)$$

wherein X and $R^6$ are as previously defined for this method and $Z^4$ is a leaving group, e.g. halo, preferably chloro, and in the presence of a Lewis acid where R is not OH and optionally in the presence of a Lewis acid where R is OH. Suitable Lewis acids include aluminium chloride and diethylaluminium chloride.

The reaction may be carried out in a suitable solvent, e.g. toluene, at from room temperature to the reflux temperature.

The preferred base salts of an indole of the formula (X) include the alkali metal and alkaline earth metal salts, e.g. the sodium and potassium salts.

Where a compound of the formula (I) wherein $R^5$ is —COOH is required the product is obtained as a base salt which may be converted to the carboxylic acid by acidification in the work-up procedure.

Where a compound of the formula (I) wherein R is OH is required an indole of the formula (IX) or a base salt of an indole of the formula (X) should first be treated with one equivalent of a suitable base, e.g. calcium hydroxide, to form an enolate salt which may then be acylated with a compound of the formula (XI), optionally in the presence of a Lewis acid. Incorporation of an acidification step in the work-up procedure affords a compound of the formula (I) wherein R is OH.

16) The compounds of the formula (I) wherein $R^5$ is —COOH, X is O, NH, N($C_1$–$C_4$ alkyl), direct link or $C_1$–$C_4$ alkylene, said alkylene being optionally substituted by $C_1$–$C_4$ alkyl or aryl, and Y, R, $R^1$ to $R^4$ and $R^6$ are as previously defined for a compound of the formula (I) may be prepared by oxidative cleavage of a compound of the formula:

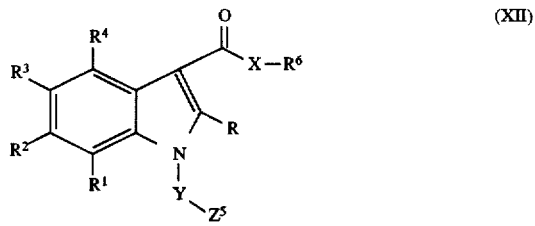

wherein $Z^5$ is —CH=$CH_2$ or —C≡CH and X, Y, R, $R^1$ to $R^4$ and $R^6$ are as previously defined for this method.

The reaction may be carried out by ozonolysis or by treatment with aqueous potassium permanganate solution.

17) The compounds of the formula (I) wherein X is O, $R^5$ is either —$COOR^7$ or —$CONR^8R^9$ and Y, R, $R^1$ to $R^4$, $R^6$, $R^7$, $R^8$ and $R^9$ are as previously defined for a compound of the formula (I) may be prepared by esterification of a compound of the formula:

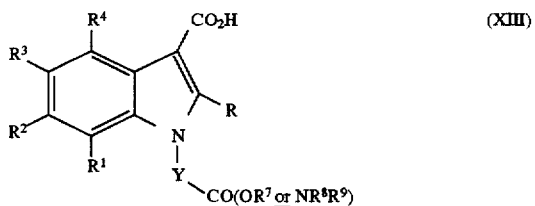

wherein Y, R, $R^1$ to $R^4$, $R^7$, $R^8$ and $R^9$ are as previously defined for this method, with a compound of the formula:

$$R^6OH \qquad (XIV)$$

wherein $R^6$ is as previously defined for this method. A similar esterification procedure to any one of those described in method (7) may be used.

18) The compounds of the formula (I) wherein X, Y, R and $R^1$ to $R^6$ are as defined for a compound of the formula (I) in method (17) may be prepared by reaction of a compound of the formula:

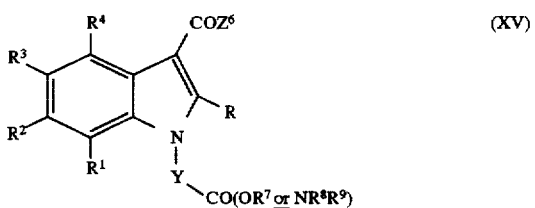

wherein Y, R, $R^1$ to $R^4$, $R^7$, $R^8$ and $R^9$ are as previously defined for this method and $Z^6$ is a leaving group, e.g. chloro or bromo, with a compound of the formula (XIV) wherein $R^6$ is as previously defined for this method.

The reaction may be carried out in the presence of an acid acceptor, e.g. pyridine, and in a suitable solvent, e.g. dichloromethane, at from 0° C. to room temperature.

19) The compounds of the formula (I) wherein X is NH or N($C_1$–$C_4$ alkyl), $R^5$ is either —$COOR^7$ or —$CONR^8R^9$ and Y, R, $R^1$ to $R^4$, $R^6$, $R^7$, $R^8$ and $R^9$ are as previously defined for a compound of the formula (I) may be prepared by reaction of a compound of the formula (XIII) wherein Y, R, $R^1$ to $R^4$, $R^7$, $R^8$ and $R^9$ are as previously defined for this method, with an amine of the formula:

$$(\text{H or } C_1\text{–}C_4 \text{ alkyl})NHR^6 \qquad (XVI)$$

wherein $R^6$ is as previously defined for this method.

The reaction may be carried out in the presence of a suitable dehydrating agent, e.g. dicyclohexylcarbodiimide, and in a suitable organic solvent, e.g. dichloromethane, at from room temperature to the reflux temperature.

Alternatively the reaction may be carried out by first forming an activated ester or imidazolide derivative of the carboxylic acid, followed by reaction of the activated ester or imidazolide in situ with the amine. Suitable procedures for the formation of an activated ester or imidazolide are described in method (7).

20) The compounds of the formula (I) wherein X, Y, R and $R^1$ to $R^6$ are as defined for a compound of the formula (I) in method (19) may be prepared by reaction of a compound of the formula (XV), wherein Y, R, $R^1$ to $R^4$, $R^7$, $R^8$ and $R^9$ are as previously defined for this method and $Z^6$ is as previously defined for a compound of the formula (XV) with an amine of the formula (XVI) wherein $R^6$ is as previously defined for this method. The reaction may be carried out in the presence of an acid acceptor, e.g. pyridine, and in a suitable solvent, e.g. dichloromethane, at from 0° C. to room temperature.

21) The compounds of the formula (I) wherein X is NH or $N(C_1$-$C_4$ alkyl), $R^5$ is —COOH or —$CONR^8R^9$ and Y, R, $R^1$ to $R^4$, $R^6$, $R^8$ and $R^9$ are as defined for a compound of the formula (I) may be prepared by reaction of a compound of the formula:

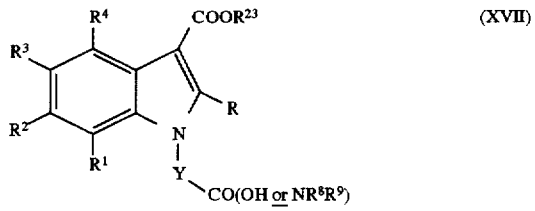

(XVII)

or a base salt thereof,
wherein Y, R, $R^1$ to $R^4$, $R^8$ and $R^9$ are as previously defined for this method and $R^{23}$ is a suitable ester-forming group, e.g. $C_1$-$C_4$ alkyl or p-nitrophenyl, with an amine of the formula (XVI) wherein $R^6$ is as previously defined for this method.

The reaction may be carried out in a suitable solvent, e.g. a $C_1$-$C_4$ alkanol, at from room temperature to the reflux temperature.

22) The compounds of the formula (I) wherein $R^5$ is —COOH and X, Y, R, $R^1$ to $R^4$ and $R^6$ are as previously defined for a compound of the formula (I) may be prepared by oxidation of a compound of the formula:

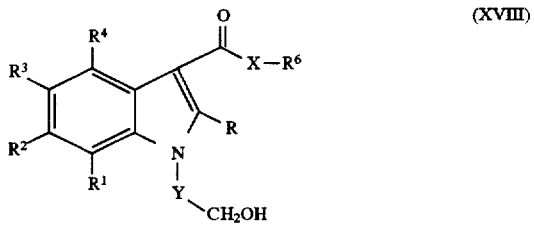

(XVIII)

wherein X, Y, R, $R^1$ to $R^4$ and $R^6$ are as previously defined for this method. A suitable oxidising agent for this purpose is chromium trioxide in pyridine.

23) The compounds of the formula (I) wherein $R^5$ is —COOH, X is direct link and Y, R, $R^1$ to $R^4$ and $R^6$ are as previously defined for a compound of the formula (I) may be prepared by oxidation of a compound of the formula:

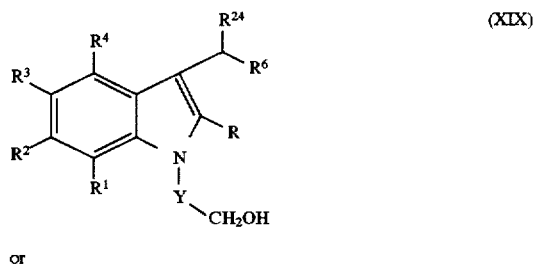

(XIX)

or

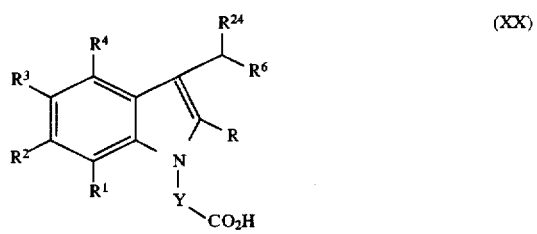

(XX)

or a base salt thereof,
wherein $R^{24}$ is H or OH and Y, R, $R^1$ to $R^4$ and $R^6$ are as defined for a compound of the formula (I). A suitable oxidising agent for this purpose is chromium trioxide-pyridine complex.

The oxidation may alternatively be carried out on a compound of the formula (XX) wherein $R^{24}$ is H using 2,3-dichloro-5,6-dicyano-1,4-benzoquinone (DDQ) as the oxidising agent.

The oxidation may alternatively be carried out on a compound of the formula (XX) wherein $R^{24}$ is OH using manganese dioxide as the oxidising agent or under the conditions of the Swern oxidation reaction.

The starting materials of the formula (XIX) or (XX) wherein $R^{24}$ is H may be prepared by reacting the corresponding 1H-indole-3-magnesium halide derivative with a compound of the formula:

$R^6CH_2 Z^7$    (XXI)

wherein $R^6$ is as previously defined for this method and $Z^7$ is halo, preferably chloro or bromo, followed by N-alkylation of the indole by a similar procedure to that described in method (14).

The starting materials of the formula (XIX) or (XX) wherein $R^{24}$ is OH may be prepared by reacting the corresponding 1H-indole-3-magnesium halide derivative with a compound of the formula:

$R^6CHO$    (XXII)

wherein $R^6$ is as previously defined for this method followed by N-alkylation of the indole by a similar procedure to that described in method (14).

24) The compounds of the formula (I) wherein X is $C_2$-$C_4$ alkylene optionally substituted by $C_1$-$C_4$ alkyl or aryl, and Y, R, $R^1$ to R and $R^6$ are as defined for a compound of the formula (I) may be prepared by reduction of a compound of the formula (I) wherein X is $C_2$-$C_4$ alkenylene or $C_2$-$C_4$ alkynylene, said alkenylene and alkynylene being optionally substituted by $C_1$-$C_4$ alkyl or aryl, and Y, R, $R^1$ to $R^4$ and $R^6$ are as previously defined for a compound of the formula (I).

The reduction may be carried out using hydrogen in the presence of a suitable catalyst, e.g. palladium-on-charcoal, and in a suitable solvent, e.g. ethanol or ethyl acetate, at from room temperature to the reflux temperature and at a pressure of from one to five atmospheres.

25) The compounds of the formula (I) wherein X, Y, R and $R^1$ to $R^6$ are as defined for a compound of the formula (I) may be prepared from a compound of the formula:

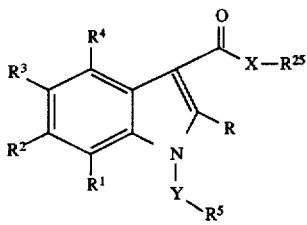 (XXIII)

wherein X, Y, R and $R^1$ to $R^5$ are as previously defined for this method and $R^{25}$ is

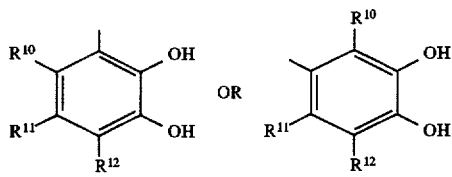

wherein $R^{10}$, $R^{11}$ and $R^{12}$ are as defined for a compound of the formula (I), by reaction with:

a) a compound of the formula:

$R^{13}R^{14}C[O(C_1-C_4 alkyl)]_2$ (XXIV)

wherein $R^{13}$ and $R^{14}$ are as defined for a compound of the formula (I). In a typical procedure the ketal or acetal (XXIV) and the compound of the formula (XXIII) are heated together under reflux in a suitable organic solvent, e.g. toluene, in the presence of a catalytic amount of a suitable acid, e.g. p-toluenesulphonic acid. Preferably the dimethyl ketal or acetal is used and the reaction is carried out in a Dean-Stark apparatus;

b) a compound of the formula:

$R^{13}R^{14}CCl_2$ (XXV)

wherein $R^{13}$ and $R^{14}$ are as previously defined for a compound of the formula (I). In a typical procedure the compounds of the formulae (XXIII) and (XXV) are heated together in the absence of solvent at about 150° C. to provide the product;

c) a compound of the formula:

$R^{13}R^{14}C[S(C_1-C_4 alkyl)]_2$ (XXVI)

wherein $R^{13}$ and $R^{14}$ are as previously defined for a compound of the formula (I). The preferred $C_1-C_4$ alkyl group in (XXVI) is methyl. In a typical procedure the compounds of the formula (XXIII) and (XXVI) are heated together in a suitable organic solvent, e.g. toluene, with mercury (II) catalysis, e.g. by using mercury (II) chloride;

d) a compound of the formula:

$R^{13}R^{14}C=(O\ or\ S)$ (XXVII)

wherein $R^{13}$ and $R^{14}$ are as defined for a compound of the formula (I). In a typical procedure the compounds of the formulae (XXIII) and (XXVII) are heated together under reflux in a suitable organic solvent, e.g. toluene, in the presence of a suitable acid catalyst, e.g. hydrochloric acid or sulphuric acid, and preferably in a Dean-Stark apparatus;

e) a compound of the formula:

$R^{13}R^{14}C=N_2$ (XXVIII)

wherein $R^{13}$ and $R^{14}$ are as defined for a compound of the formula (I). The reaction is typically carried out in a suitable aprotic organic solvent, e.g. dichloromethane, at room temperature and in the presence of t-butyl hypochlorite. The compounds of the formula (XXVIII) may be prepared from the corresponding hydrazone derivatives by oxidation; or f) , for compounds of the formula (I) wherein in $R^6$ at least one of $R^{13}$ and $R^{14}$, or when $R^{13}$ and $R^{14}$ taken together with the carbon atom to which they are attached represent a spiro group, the spiro group, has a hydrogen atom in the α-position with respect to the position of attachment to the 1,3-benzodioxolane ring, an enol ether derivative of a compound of the formula:

$R^{13}R^{14}C=O$ (XXVIIA)

wherein $R^{13}$ and $R^{14}$ are as defined for this procedure (f). The reaction is typically carried out in a suitable organic solvent, e.g. toluene, in the presence of an acid catalyst, e.g. p-toluenesulphonic, hydrochloric or sulphuric acid, at from room temperature to the reflux temperature of the solvent. Suitable enol ether derivatives for use in this procedure (f) may be derived from a compound of the formula (XXVIIA) by reaction with a suitable tri($C_1-C_4$ alkyl)orthoformate, e.g. trimethylorthoformate, in the presence of an acid catalyst, e.g. p-toluenesulphonic acid.

To prepare a compound of the formula (I) wherein $R^5$ is —COOH, any one of methods (25)(a) to (f) may also be carried out using a suitable base, e.g. sodium, salt of a compound of the formula (XXIII) wherein $R^5$ is —COOH, i.e. a carboxylate salt, followed by an acidification step in the work-up procedure.

The starting materials of the formula (XXIII) may be prepared by acidic hydrolysis of a compound of the formula (I) wherein $R^{13}$ and $R^{14}$ are both phenyl and otherwise $R^6$ and X, Y, R and $R^1$ to $R^5$ are as defined for a compound of the formula (I). In a typical procedure the hydrolysis is carried out using aqueous acetic acid and the reaction is heated under reflux.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The compounds of the formula (I) are steroid 5α-reductase inhibitors and therefore they are useful in the curative or prophylactic treatment of diseases or conditions such as acne vulgaris, alopecia, seborrhoea, female hirsutism, benign prostatic hypertrophy and male pattern baldness.

Certain compounds of the formula (I) are also useful for the treatment of human prostate adenocarcinomas.

The compounds of the formula (I) may be tested in vitro for steroid 5α-reductase inhibitory activity using prostate tissue from rats or humans as follows:

(i) The compounds of the formula (I) may be tested for their potency in inhibiting rat steroid 5α-reductase using ventral prostate tissue from male rats. In determining inhibitory potency against rat prostatic 5α-reductase the following procedure was employed:

Rat prostates were minced into small pieces. The tissue was homogenised in Buffer A (20 mM sodium phosphate, pH 6.5, buffer containing 0.32M sucrose and 1 mM dithiothreitol) with a Brinkman Polytron (Kinematica, Luzern, GmBH), and then homogenised with a motor driven (1000 rpm) Potter Elvehjem (teflon-to-glass) homogeniser. Prostate particles were obtained by centrifugation at 105,000 G for 60 minutes. The pellet was washed in 4 volumes of Buffer A and recentrifuged at 105,000 G. The resulting pellet was dispersed in Buffer A (1 ml per g of prostate tissue originally used) with a motor driven Potter Elvehjem homogeniser as described above. The particulate suspension was stored as 1 ml samples at −70° C.

The following components, dissolved in Buffer B (40 mM sodium phosphate buffer, pH 6.5), were added to test tubes: 500 µl of [$^3$H]-testosterone (1 µCi, 1 nmol; Du Pont, NEN Research Products, Stevenage, U.K.), 100 µl of 0.5 mM NADPH, a compound of the formula (I) dissolved in 5 µl of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and then quenched by addition with vigorous mixing of 2 ml of ethyl acetate containing 20 µg each of testosterone and 5α-dihydrotestosterone as carriers. The aqueous and organic layers were separated by centrifugation at 2000 G for 10 minutes. The organic layer was transferred to a second test tube and evaporated to dryness under nitrogen. The residue was dissolved in 50–80 µl of absolute ethanol and spotted onto a silica gel 60 F254 TLC plate (E. Merck, Darmstadt, Germany) and developed in chloroform:acetone (185:15).

The radiochemical content in the bands of the substrate (testosterone) and the product (5α-dihydrotestosterone) were determined with a RITA Radio TLC Analyser (Raytest Instruments Ltd., Sheffield, U.K.). The percent of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard, D., American Journal of Physiology, 235, E97 (1978)).

(ii) The compounds of the formula (I) may be tested for their potency in inhibiting human steroid 5α-reductase using tissue from hyperplastic human prostates. In determining inhibitory potency against human prostatic 5α-reductase the following procedure was employed:

Frozen human prostate tissue was pulverised in liquid nitrogen using a steel mortar and pestle. The powdered tissue was homogenised in 4 volumes of Buffer A (20 mM sodium phosphate, pH 6.5, containing 0.32M sucrose, 1 mM dithiothreitol and 50 µM NADPH) with an Ultra-Turrax (Janke and Kunkel GmBH & Co., Staufen i.BR., Germany). The homogenate was centrifuged at 500 G for 5 minutes, to remove large particles of tissue, and the supernatant was then centrifuged at 100,000 G for 1 hour. The resulting pellet was dispersed in Buffer A (1 ml per g of prostate tissue originally used) with the Ultra-Turrax homogeniser. This particulate preparation was then filtered through 2 layers of cheesecloth and the filtrate was stored as 1 ml samples at −70° C.

The following components, dissolved in Buffer B (20 mM citrate phosphate buffer, pH 5.2), were added to test tubes: 500 µl of [$^3$H]-testosterone (1 µCi, 1 nmol; Du Pont, NEN Research Products, Stevenage, U.K.), 100 µl of NADPH regeneration system (5 mM NADPH, 50 mM glucose 6-phosphate, 5 units/ml glucose 6-phosphate dehydrogenase), a compound of the formula (I) dissolved in 5 µl of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and then quenched by addition with vigorous mixing of 2 ml of ethyl acetate containing 20 µg each of testosterone and 5α-dihydrotestosterone as carriers. The aqueous and organic layers were separated by centrifugation at 2000 G for 10 minutes. The organic layer was transferred to a second test tube and evaporated to dryness under nitrogen. The residue was dissolved in 50–80 µl of absolute ethanol and spotted onto a silica gel 60 F254 TLC plate (E. Merck, Darmstadt, Germany) and developed in chloroform:acetone (185:15).

The radiochemical content in the bands of the substrate (testosterone) and the product (5α-dihydrotestosterone) were determined with a RITA Radio TLC Analyser (Raytest Instruments Ltd., Sheffield, U.K.). The percent of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard, D., American Journal of Physiology, 235, E97 (1978)).

The compounds of the formula (I) may be tested for potency in inhibiting steroid 5α-reductase activity in human prostate adenocarcinomas using cell lines DU145 and HPC36M. In determining inhibitory potency against 5α-reductase the following procedure was employed: Human prostate adenocarcinoma cell lines were grown in Dulbecco's Modified Eagles medium (DMEM) containing 5% serum. The cells were recovered from the medium by centrifugation, washed in serum free DMEM and suspended at 5-10×10$^6$ cells/ml. in serum free medium.

The following components were added to a test tube: 10 µl of [$^3$H]-testosterone (1 µCi, 20 pmol) dissolved in ethanol (Du Pont, NEN Research Products, Stevenage, U.K.) and 5 µl of an ethanol solution of a compound of the formula (I). The ethanol was evaporated under nitrogen and the testosterone and the compound redissolved in 0.25 ml of serum free medium containing 0.25 µmol NADPH. The mixture was warmed to 37° C. and the reaction started by addition of 0.25 ml of cell suspension (1.2-2.5×10$^6$ cells). The reaction mixture was incubated at 37° C. for 2 hours and then quenched by addition with vigorous mixing of 1.5 ml of ethyl acetate containing 20 μg each of testosterone and 5α-dihydrotestosterone as carriers. The aqueous and organic layers were separated by centrifugation at 2000 G for 10 minutes. The organic layer, containing testosterone and its metabolites, was transferred to a second test tube and evaporated to dryness under nitrogen. The residue was dissolved in 50–80 μl of absolute ethanol, spotted onto a silica gel 60 F254 TLC plate (E. Merck, Darmstadt, Germany) and developed in dichloromethane:acetone (185:15).

The radiochemical content in the bands of the substrate (testosterone) and the product (5α-dihydrotestosterone) was determined with a RITA Radio TLC Analyser (Raytest Instruments Ltd., Sheffield, U.K.). The percentage of recovered radiolabel converted to 5α-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard D., American Journal of Physiology, 235, E97 (1978)).

For human use, the compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions of suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses) and preferably will be from 0.1 to 10 mg/kg except for the treatment of human prostate adenocarcinomas where doses of up to 20 mg/kg may be used. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) may also be administered together with an α-antagonist (e.g. prazosin or doxazosin), an antiandrogen (e.g. flutamide) or an aromatase inhibitor (e.g. atamestane), particularly for the curative or prophylactic treatment of benign prostatic hypertrophy.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for inhibiting a steroid 5α-reductase;

iv) the use of a compound of the formula (I), or of a pharmaceutically acceptable salt or composition thereof, for the manufacture of a medicament for the curative or prophylactic treatment of acne vulgaris, alopecia, seborrhoea, female hirsutism, benign prostatic hypertrophy, male pattern baldness or a human prostate adenocarcinoma;

v) a method of treatment of a human to inhibit a steroid 5α-reductase which comprises treating said human with an effective amount of a compound of the formula (I) or with a pharmaceutically acceptable salt or composition thereof;

vi) a method of treatment of a human to cure or prevent acne vulgaris, alopecia, seborrhoea, female hirsutism, benign prostatic hypertrophy male pattern baldness or a human prostate adenocarcinoma which comprises treating said human with an effective amount of a compound of the formula (I) or with a pharmaceutically acceptable salt or composition thereof; and vii) intermediates of the formulae (III), (IV), (VIII) or a base salt thereof, (XVIII), (XIX), (XX) or a base salt thereof and (XXIII).

The following Examples illustrate the preparation of the compounds of the formula (I):

EXAMPLE 1

4-[3-(2,2-Diphenyl-1,3-benzodioxolan-5-yl]-carbonyl)indol-1-yl]butanoic acid

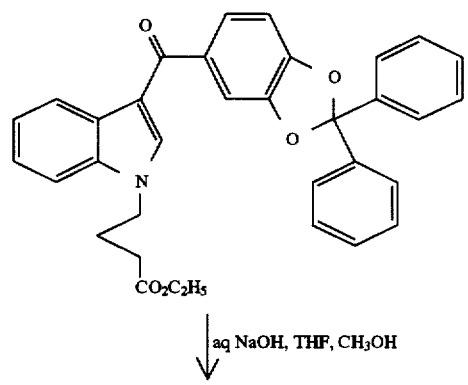

5,767,139

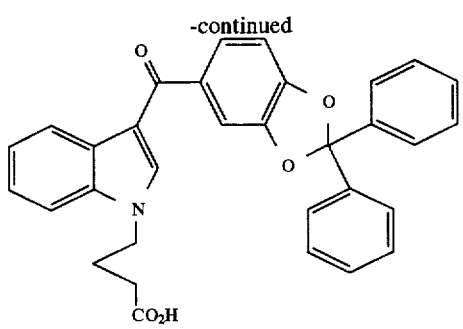

A suspension of ethyl 4-[3-([2,2-diphenyl-1,3-benzodioxolan-5-yl]carbonyl)indol-1-yl]butanoate (2.6 g) (see Example 48) in tetrahydrofuran (THF) (10 ml) and methanol (10 ml) was treated with 2N aqueous sodium hydroxide (10 ml) and heated at reflux for 10 minutes. The mixture was cooled, cautiously concentrated in vacuo, cooled in an ice-bath and acidified with 2N aqueous hydrochloric acid. The acid phase was extracted with diethyl ether (100 ml), the organic extract dried (magnesium sulphate), filtered and concentrated in vacuo to give the title compound as a pale yellow foam (2.3 g). Recrystallisation from ethyl acetate gave fine white clusters of needles, m.p. 214.5°–214.8° C. Found: C, 76.41; H, 5.06; N, 3.01; $C_{32}H_{25}NO_5$ requires: C, 76.33; H, 5.00; N, 2.78%.

$^1$H-NMR (CDCl$_3$): δ=2.20 (m,2H), 2.40 (t,2H), 4.20 (t,2H); 6.95(d,1H), 7.25–7.40 (m,11H), 7.55–7.62 (m,5H), 8.40 (m,1H) ppm.

EXAMPLES 2 to 47

The following compounds of the general formula:

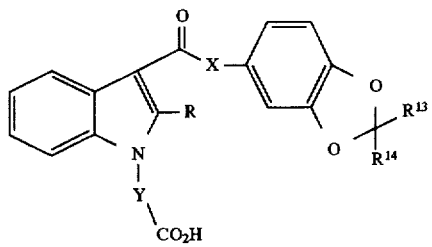

or base salts thereof, were prepared by hydrolysis of the corresponding ethyl esters (see Examples 49 to 93) by similar methods to that used in Example 1.

| Ex. No. | X | Y | R | R$^{13}$ | R$^{14}$ | m/z | Analysis/$^1$H-NMR/HPLC/Rotation |
|---|---|---|---|---|---|---|---|
| 2[1] | direct link | (CH$_2$)$_3$ | H | CH$_3$ | 4-methylbenzyl-CH(CH$_3$)- (CH$_3$) | — | Found: C, 75.05; H, 6.43; N, 2.80; C$_{31}$H$_{31}$NO$_5$ requires: C, 74.83; H, 6.28; N, 2.82%. $^1$H-NMR (d$_6$-DMSO): δ = 0.85 (d,6H), 1.80 (m,1H), 2.00 (m,5H), 2.20 (m,2H), 2.45 (d,2H), 4.30 (m,2H), 7.05 (d,1H), 7.20–7.40 (m,6H), 7.50 (d,2H), 7.62 (d,1H), 8.05 (s,1H), 8.25 (d,1H), 12.40 (s,br,1H) ppm. |
| 3[2] | direct link | (CH$_2$)$_3$ | H | CH$_3$ | 4-methylbenzyl-CH(CH$_3$)- (CH$_3$) | 498 (m+1)$^+$ | Product obtained as a single enantiomer. Found: C, 74.34; H, 6.30; N, 2.84; C$_{31}$H$_{31}$NO$_5$ requires: C, 74.83; H, 6.28; N, 2.82%. [α]$_D^{25}$ + 119° (c = 0.1 in methanol) $^1$H-NMR (d$_6$-DMSO): Identical to Example 2. HPLC (CHIRALPAK AD, Trade Mark): Eluant = hexane (80%)/ethanol + 0.1% trifluoroacetic acid (20%) at a flow rate of 1.0 ml/min., RT = 12.37 (99%). |
| 4[3] | direct link | (CH$_2$)$_3$ | H | CH$_3$ | 4-methylbenzyl-CH(CH$_3$)- (CH$_3$) | 498 (m+1)$^+$ | Product obtained as a single enantiomer. Found: C, 74.76; H, 6.42; N, 2.99; C$_{31}$H$_{31}$NO$_5$ requires: C, 74.83; H, 6.28; N, 2.82%. [α]$_D^{25}$ − 125° (c = 0.1 in methanol) $^1$H-NMR (d$_6$-DMSO): identical to Example 2. HPLC (CHIRALPAK AD, Trade Mark): Eluant = hexane (80%)/ethanol + 0.1% trifluoroacetic acid (20%) at a flow rate of 1.0 ml/min., RT = 9.29 (98.2%). |

-continued

| Ex. No. | X | Y | R | R¹³ | R¹⁴ | m/z | Analysis/¹H-NMR/HPLC/Rotation |
|---|---|---|---|---|---|---|---|
| 5 | direct link | $(CH_2)_3$ | H | 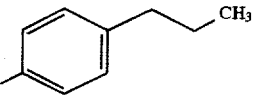 | 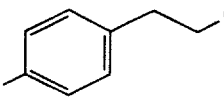 | 587 (m+) | Found: C, 77.88; H, 6.51; N, 2.39; $C_{38}H_{37}NO_5$ requires: C, 77.66; H, 6.35; N, 2.38%. ¹H-NMR (CDCl₃): δ = 0.90 (t,6H), 1.62 (m,4H), 2.20 (m,2H), 2.39 (t,2H), 2.60 (m,4H), 4.25 (t,2H), 6.90 (d,1H), 7.18–7.40 (m,9H), 7.50 (d,4H), 7.58 (s,1H), 8.35 (m,1H), ppm. |
| 6 | direct link | $(CH_2)_3$ | H | 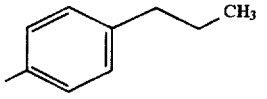 | 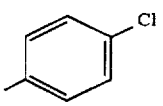 | 572 (m+) | ¹H-NMR (d₆-DMSO): δ = 1.90 (m,2H), 2.05 (t,2H), 4.20 (t,2H), 7.15–7.25 (m,3H), 7.40–7.65 (m,11H), 8.00 (s,1H), 8.20 (d,1H) ppm. |
| 7 | direct link | $(CH_2)_3$ | H | 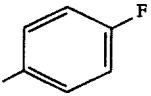 | 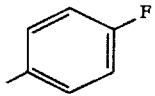 | 540 (m+1)⁺ | Found: C, 68.79; H, 4.01; N, 2.52; $C_{32}H_{23}F_2NO_5 \cdot H_2O$ requires: C, 68.94; H, 4.16; N, 2.51%. ¹H-NMR (d₆-DMSO): δ = 1.90 (m,2H), 2.05 (t,2H), 4.20 (t,2H), 7.15 (d,1H), 7.19–7.25 (m,8H), 7.40–7.60 (m,5H), 8.00 (s,1H), 8.20 (d,1H) ppm. |
| 8 | direct link | $(CH_2)_3$ | H | —$(CH_2)_3CH_3$ | 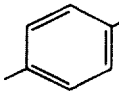 | 525 (m+) | Found: C, 74.02; H, 6.29; N, 2.48; $C_{33}H_{35}NO_5 \cdot 1/2H_2O$ requires: C, 74.13; H, 6.60; N, 2.62%. ¹H-NMR (CDCl₃): δ = 0.85 (t,3H), 0.93 (t,3H), 1.30–1.50 (m,4H), 1.60 (m,2H), 2.15–2.25 (m,4H), 2.38 (t,2H), 2.58 (t,2H), 4.25 (t,2H), 6.82 (d,1H), 7.18 (d,2H), 7.30–7.40 (m,5H), 7.48 (d,2H), 7.60 (s,1H), 8.37 (m,1H) ppm. |
| 9 | direct link | $(CH_2)_3$ | H | CH₃ |  | 548 (m+1)⁺ | Found: C, 74.18; H, 5.17; N, 2.25; $C_{34}H_{29}NO_6$ requires: C, 74.57; H, 5.34; N, 2.56%. ¹H-NMR (CDCl₃): δ = 2.02 (s,3H), 2.20 (m,2H), 2.38 (t,2H) 4.25 (t,2H), 5.05 (s,2H), 6.85(d,1H), 6.95 (d,2H), 7.30–7.58 (m,13H), 8.37(m,1H) ppm. |
| 10 | direct link | $(CH_2)_3$ | H | | 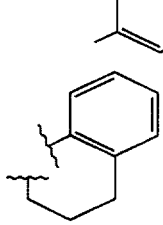 | 468 (m+1)⁺ | Found: C, 68.92; H, 4.84; N, 2.55; $C_{29}H_{25}NO_5 \cdot 2H_2O$ requires: C, 69.17; H, 5.00; N, 2.78%. ¹H-NMR (CDCl₃): δ = 2.05–2.45 (m,8H), 2.90 (t,2H), 4.30 (t,2H), 6.85 (d,1H), 7.18–7.44 (m,8H), 7.55 (d,1H), 7.60 (s,1H), 8.40 (m,1H) ppm. |
| 11 | direct link | $(CH_2)_3$ | H | |  | 491 (m+Na)⁺ | Product isolated as the sodium salt of the acid. Found: C, 69.95; H, 4.74; N, 2.64; $C_{29}H_{24}NO_5Na \cdot 1/2H_2O$ requires: C, 69.87; H, 5.05; N, 2.81%. ¹H-NMR (CDCl₃): δ = 2.20 (m,2H), 2.30 (m,2H), 2.38 (t,2H), 3.10 (t,2H), 3.35 (s,2H), 4.25 (t,2H), 6.82 (d,1H), 7.10–7.40 (m,8H), 7.60 (s,1H), 8.40 (m,1H) ppm. |

-continued

| Ex. No. | X | Y | R | R¹³ | R¹⁴ | m/z | Analysis/¹H-NMR/HPLC/Rotation |
|---|---|---|---|---|---|---|---|
| 12 | direct link | (CH$_2$)$_3$ | H | | cyclohexyl | 420 (m+1)⁺ | Found: C, 71.74; H, 6.08; N, 3.11; C$_{25}$H$_{25}$NO$_5$ requires: C, 71.58; H, 6.01; N, 3.34%. ¹H-NMR (CDCl$_3$): δ = 1.50 (m,2H), 1.75 (m,4H), 1.97 (m,4H), 2.21 (m,2H), 2.40 (t,2H), 4.30 (t,2H), 6.80 (d,1H), 7.30–7.41 (m,5H), 7.60 (s,1H), 8.40 (m,1H) ppm. |
| 13 | direct link | (CH$_2$)$_3$ | H | | cycloheptyl | 434 (m+1)⁺ | Found: C, 70.61; H, 6.34; N, 2.82; C$_{26}$H$_{27}$NO$_5$.1/2H$_2$O requires: C, 70.57; H, 6.38; N, 3.17%. ¹H-NMR (CDCl$_3$): δ = 1.65 (s,br,8H), 2.18 (s,br,4H), 2.20 (m,2H), 2.40 (t,2H), 4.30 (t,2H), 6.80 (d,1H), 7.30–7.42 (m,5H), 7.60 (s,1H), 8.40 (m,1H) ppm. |
| 14 | direct link | (CH$_2$)$_3$ | H | CH$_3$ | phenyl | 442 (m+1)⁺ | Found: C, 68.74; H, 4.91; N, 2.73; C$_{27}$H$_{23}$NO$_5$.3/2H$_2$O requires: C, 69.22; H, 4.95; N, 2.99%. ¹H-NMR (CDCl$_3$): δ = 2.02 (s,3H), 2.20 (m,2H), 2.39 (t,2H), 4.25 (t,2H), 6.85 (d,1H), 7.30–7.45 (m,8H), 7.60 (s,1H), 7.62 (d,2H), 8.40 (m,1H) ppm. |
| 15 | direct link | (CH$_2$)$_3$ | H | 2-thienyl | 2-thienyl | 515 (m+) | Found: C, 64.90; H, 4.20; N, 2.67; C$_{28}$H$_{21}$NO$_5$S$_2$ requires: C, 65.23; H, 4.11; N, 2.72%. ¹H-NMR (CDCl$_3$): δ = 2.20 (m,2H), 2.40 (t,2H), 4.30 (t,2H), 6.95 (d,1H), 7.00 (m,1H), 7.30–7.50 (m,10H), 7.60 (s,1H), 8.40 (m,1H) ppm. |
| 16 | direct link | (CH$_2$)$_3$ | H | 2-furyl | 2-furyl | 484 (m+1)⁺ | Found: C, 67.90; H, 4.43; N, 3.08; C$_{28}$H$_{21}$NO$_7$.1/2H$_2$O requires: C, 68.30; H, 4.30; N, 2.84%. ¹H-NMR (CDCl$_3$): δ = 2.24 (m,2H), 2.40 (t,2H), 4.30 (t,2H), 6.42 (m,2H), 6.65 (m,2H), 6.95 (m,2H), 7.30–7.60 (m,7H), 8.38 (m,1H) ppm. |
| 17 | direct link | (CH$_2$)$_3$ | H | | 1-cyano-1-phenyl-cyclohexyl | 521 (m+1)⁺ | Found: C, 74.12; H, 5.45; N, 5.34; C$_{32}$H$_{28}$N$_2$O$_5$ requires: C, 73.83; H, 5.42; N, 5.38%. ¹H-NMR (CDCl$_3$): δ = 2.10–2.50 (m,12H), 4.20 (t,2H), 6.80 (d,1H), 7.20–7.60 (m,11H), 8.30 (m,1H) ppm. |
| 18 | direct link | (CH$_2$)$_3$ | H | —(CH$_2$)$_2$CH$_3$ | —(CH$_2$)$_2$CH$_3$ | 436 (m+1)⁺ | Found: C, 71.79; H, 6.70; N, 2.99; C$_{26}$H$_{29}$NO$_5$ requires: C, 71.70; H, 6.71; N, 3.22%. ¹H-NMR (CDCl$_3$): δ = 0.90 (t,6H), 1.40 (m,4H), 1.85 (m,4H), 2.15 (m,2H), 2.35 (t,2H), 4.20 (t,2H), 6.70 (d,1H), 7.20–7.40 (m,5H), 7.55 (s,1H), 8.35 (m,1H), 9.35 (s,br,1H) ppm. |

-continued

| Ex. No. | X | Y | R | R13 | R14 | m/z | Analysis/1H-NMR/HPLC/Rotation |
|---|---|---|---|---|---|---|---|
| 19 | direct link | (CH2)3 | H | CH3 | 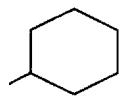 | 448 (m+1)+ | Found: C, 72.09; H, 6.39; N, 2.84; C27H29NO5 requires: C, 72.46; H, 6.53; N, 3.13%. 1H-NMR (CDCl3): δ = 1.00–1.25 (m,5H), 1.55 (s,3H), 1.56–1.90 (m,6H), 2.15 (m,2H), 2.35 (t,2H), 4.20 (t,2H), 6.70 (d,1H), 7.20–7.35 (m,5H), 7.55 (s,1H), 8.30 (m,1H) ppm. |
| 20 | direct link | (CH2)3 | H | CH3 | 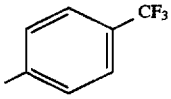 | 511 (m+1)+ | Found: C, 66.12; H, 4.20; N, 2.51; C28H22NO5F3 requires: C, 66.01; H, 4.35; N, 2.75%. 1H-NMR (CDCl3): δ = 2.00 (s,3H); 2.20 (m,2H), 2.40 (t,2H), 4.25 (t,2H), 6.85 (d,1H), 7.30–7.40 (m,5H), 7.55 (s,1H), 7.65 (d,2H), 7.75 (d12H), 8.35 (m,1H) ppm. |
| 21 | direct link | (CH2)3 | H | CH3 | 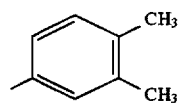 | 470 (m+1)+ | Found: C, 74.26; H, 5.91; N, 2.64; C29H27NO5 requires: C, 74.18; H, 5.80; N, 2.98%. 1H-NMR (CDCl3): δ = 2.00 (s,3H), 2.20 (m,2H), 2.24 (s,3H), 2.30 (s,3H), 2.38 (t,2H), 4.15 (t,2H), 6.85 (d,1H), 7.15 (d,1H), 7.30–7.40 (m,7H), 7.60 (s,1H), 8.35 (m,1H) ppm. |
| 22 | direct link | (CH2)3 | H | CH3 | 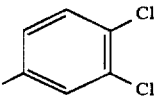 | 511 (m+1)+ | Found: C, 63.64; H, 4.08; N, 2.53; C27H21NO5Cl2 requires: C, 63.53; H, N, 2.53; C27H21NO5Cl2 requires: C, 63.53; H, 4.15; N, 2.74%. 1H-NMR (CDCl3): δ = 2.00 (s,3H), 2.20 (m,2H), 2.40 (t,2H), 4.25 (t,2H), 6.90 (d,1H), 7.30–7.50 (m,7H), 7.60 (s,1H), 7.70 (s,1H), 8.35 (s,1H) ppm. |
| 23 | direct link | (CH2)3 | H | 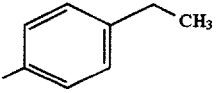 | 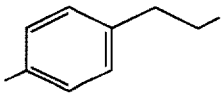 | 574 (m+1)+ | 1H-NMR (CDCl3): δ = 0.95 (t,3H), 1.20 (t,3H), 1.60 (m,2H), 2.20 (m,2H), 2.38 (t,2H), 2.59 (t,2H), 2.65 (t,2H), 4.25 (t,2H), 6.90 (d,1H), 7.20–7.55 (m,14H), 8.35 (m,1H) ppm. |
| 24 | direct link | (CH2)3 | H | 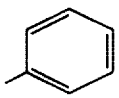 | 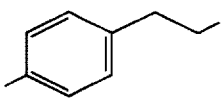 | 545 (m+) | Found: C, 76.73; H, 5.61; N, 2.27; C35H31NO5 requires: C, 77.04; H, 5.73; N, 2.57%. 1H-NMR (CDCl3): δ = 0.90 (t,3H), 1.58–1.75 (m,2H), 2.20 (m,2H), 2.38 (t,2H), 2.60 (t,2H), 4.22 (t,2H), 6.90 (d,1H), 7.20 (d,2H), 7.25–7.60 (m,13H), 8.35 (m,1H) ppm. |
| 25 | direct link | (CH2)3 | H | 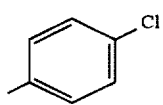 | 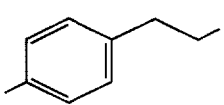 | 579 (m+) | 1H-NMR (CDCl3): δ = 0.95 (t,3H), 1.60 (m,2H), 2.20 (m,2H), 2.35 (t,2H), 2.60 (m,2H), 4.25 (t,3H), 6.90 (d,1H), 7.20 (d,2H), 7.25–7.59(m,11H), 8.35 (m,1H) ppm. |
| 26 | direct link | (CH2)3 | H | CH3 | —C(CH3)3 | 394 (m+1)+ | Found: C, 69.71; H, 6.75; N, 2.88; C25H27NO5.½H2O |

5,767,139

-continued

| Ex. No. | X | Y | R | R¹³ | R¹⁴ | m/z | Analysis/¹H-NMR/HPLC/Rotation |
|---|---|---|---|---|---|---|---|
| | | | | | | | requires: C, 69.75; H, 6.56; N, 3.25%. ¹H-NMR (CDCl₃): δ = 1.10 (s,9H), 1.60 (s,3H), 2.20 (m,2H), 2.40 (t,2H), 4.25 (t,2H), 6.80 (d,1H), 7.25–7.45 (m,5H), 7.60 (s,1H), 8.45 (m,1H) ppm. |
| 27 | direct link | (CH₂)₃ | H | —CH₂CH₃ | 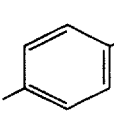 | 498 (m+1)⁺ | Found: C, 74.95; H, 6.18; N, 2.68; C₃₁H₃₁NO₅ requires: C, 74.83; H, 6.28; N, 2.81%. ¹H-NMR (CDCl₃): δ = 0.90 (t,3H), 1.05 (t,3H), 1.60 (m,2H), 2.18–2.40 (m,6H), 2.60 (t,2H), 4.25 (t,2H), 6.85 (s,1H), 7.20–7.40 (m,7H), 7.45 (d,2H), 7.60 (s,1H), 8.45 (m,1H) ppm. |
| 28 | direct link | (CH₂)₃ | H | CH₃ | 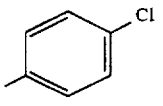 | 476 (m+) | Found: C, 68.48; H, 4.57; N, 2.67; C₂₇H₂₂NO₅Cl requires: C, 68.13; H, 4.66; N, 2.94%. ¹H-NMR (CDCl₃): δ = 2.00 (s,3H), 2.20 (m,2H), 2.38 (t,2H), 4.25 (t,2H), 6.85 (d,1H), 7.30–7.45 (m,7H), 7.55 (s,1H), 7.66 (d,2H), 8.40 (m,1H) ppm. |
| 29 | direct link | (CH₂)₃ | H | CH₃ | 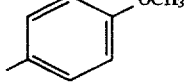 | 472 (m+1)⁺ | Found: C, 71.00; H, 5.33; N, 2.67; C₂₃H₂₅NO₆ requires: C, 71.32; H, 5.34; N, 2.97%. ¹H-NMR (CDCl₃): δ = 2.00 (s,3H), 2.20 (m,2H), 2.38 (t,2H), 3.80 (s,3H), 4.25 (t,2H), 6.85 (d,1H), 6.90 (d,2H), 7.30–7.40 (m,5H), 7.50 (d,2H), 7.55 (s,1H), 8.40 (m,1H) ppm. |
| 30 | direct link | (CH₂)₃ | H | H | 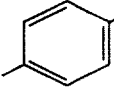 | 470 (m+1)⁺ | Found: C, 73.29; H, 5.31; N, 2.82; C₂₉H₂₆NO₅.1/2H₂O requires: C, 72.80; H, 5.60; N, 2.90%. ¹H-NMR (CDCl₃): δ = 0.95 (t,3H), 1.60–1.70 (m,2H), 2.25 (m,2H), 2.40 (t,2H), 2.63 (t,2H), 3.45 (s,br,2H), 4.25 (t,2H), 6.90 (d,1H), 7.02 (s,1H), 7.25–7.50 (m,8H), 7.60 (s,1H), 8.40 (m,1H) ppm. |
| 31 | direct link | (CH₂)₃ | H | | 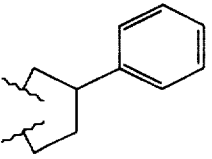 | 481 (m+) | Found: C, 73.65; H, 5.68; N, 2.57; C₃₀H₂₇NO₅.1/2H₂O requires: C, 73.45; H, 5.55; N, 2.86%. ¹H-NMR (CDCl₃): δ = 1.90–2.05 (m,1H), 2.10–2.51 (m,8H), 2.60–2.66 (m,1H), 3.38–3.42 (m,1H), 4.25 (t,2H), 6.85 (d,1H), 7.25–7.40 (m,10H), 7.60 (s,1H), 8.38 (m,1H) ppm. |

-continued

| Ex. No. | X | Y | R | R13 | R14 | m/z | Analysis/1H-NMR/HPLC/Rotation |
|---|---|---|---|---|---|---|---|
| 32 | direct link | (CH2)3 | H | 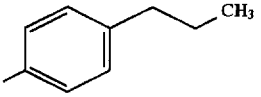 | 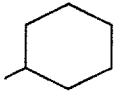 | — | Found: C, 75.61; H, 6.82; N, 2.46; $C_{35}H_{37}NO_5 \cdot 1/4H_2O$ requires: C, 75.58; H, 6.71; N, 2.52%. 1H-NMR (CDCl3): δ = 0.95 (t,3H), 1.10–1.30 (m,6H), 1.60–1.70 (m,2H), 1.70–1.85 (m,4H), 2.10–2.25 (m,3H), 2.40 (t,2H), 2.58 (t,2H), 4.25 (t,2H), 6.80 (d,1H), 7.18–7.42 (m,9H), 7.58 (s,1H), 8.38 (m,1H) ppm. |
| 33 | direct link | (CH2)2 | H | 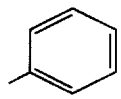 | 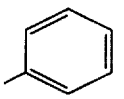 | 489 (m+) | 1H-NMR (d6-DMSO): δ = 2.80 (t,2H), 4.45 (t,2H), 6.90 (d,1H), 7.30–7.40 (m,11H), 7.50–7.59 (m,4H), 7.70 (s,1H), 8.35 (m,1H) ppm. |
| 34 | direct link | (CH2)4 | H | 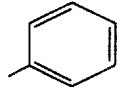 | 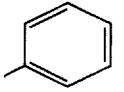 | — | Found: C, 76.73; H, 5.15; N, 2.71; $C_{33}H_{27}NO_5$ requires: C, 76.58; H, 5.26; N, 2.71%. 1H-NMR (CDCl3): δ = 1.70 (m,2H), 1.90 (m,2H), 2.40 (t,2H), 4.20 (t,2H), 6.95 (d,1H), 7.30–7.45 (m,10H), 7.60–7.70 (m,6H), 8.40 (m,1H) ppm. |
| 35 | CH2 | (CH2)3 | H | 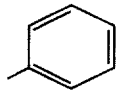 | 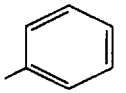 | — | Found: C, 76.67; H, 5.06; N, 2.65; $C_{33}H_{27}NO_5$ requires: C, 76.58; H, 5.26; N, 2.71%. 1H-NMR (CDCl3): δ = 2.15 (m,2H), 2.30 (t,2H), 4.00 (s,2H), 4.25 (t,2H), 6.75–6.82 (m,2H), 6.90 (s,1H), 7.20–7.40 (m,10H), 7.45–7.50 (m,3H), 7.80 (s,1H), 8.35 (m,1H) ppm. |
| 36 | CH2 | (CH2)3 | H | CH3 | 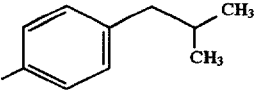 | 512 (m+1)+ | Found: C, 74.74; H, 6.40; N, 2.38; $C_{32}H_{33}NO_5$ requires: C, 75.12; H, 6.50; N, 2.73%. 1H-NMR (CDCl3): δ = 0.90 (d,6H), 1.82 (m,1H), 1.95 (s,3H), 2.20 (m,2H), 2.38 (t,2H), 2.42 (d,2H), 4.00 (s,2H), 4.22 (t,2H), 6.75 (s,2H), 6.82 (s,1H), 7.10 (d,2H), 7.20–7.40 (m,3H), 7.45 (d,2H), 7.75 (s,1H), 8.40 (m,1H) ppm. |
| 37 | CH2 | (CH2)3 | H | 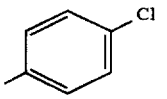 |  | 586 (m+) | Found: C, 67.36; H, 3.93; N, 2.07; $C_{33}H_{25}Cl_2NO_5$ requires: C, 67.58; H, 4.30; N, 2.39%. 1H-NMR (CDCl3): δ = 2.20 (m,2H), 2.35 (t,2H), 4.05 (s,2H), 4.25 (t,2H), 6.80 (s,2H), 6.90 (s,1H), 7.25–7.40 (m,9H), 7.45 (d,2H), 7.80 (s,1H), 8.40 (m,1H) ppm. |

-continued

| Ex. No. | X | Y | R | R¹³ | R¹⁴ | m/z | Analysis/¹H-NMR/HPLC/Rotation |
|---|---|---|---|---|---|---|---|
| 38 | direct link | (CH₂)₃ | H | 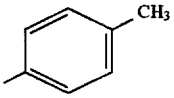 CH₃ | 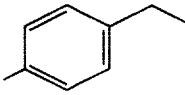 CH₃ | 560 (m+1)⁺ | Found: C, 75.00; H, 5.73; N, 2.26; C₃₆H₃₃NO₅.H₂O requires: C, 74.85; H, 6.11; N, 2.42%. ¹H-NMR (CDCl₃): δ = 0.90 (t,3H), 1.50–1.65 (m,2H), 2.15 (t,3H), 2.30 (s,3H), 2.32 (t,2H), 2.52 (t,2H), 4.20 (t,2H), 6.85 (d,1H), 7.15 (d,4H), 7.24–7.45 (m,9H), 7.50 (s,1H), 8.30 (m,1H) ppm. |
| 39* | direct link | (CH₂)₃ | CH₃ | 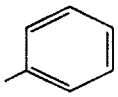 | 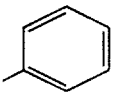 | 548 (mNa)⁺ | Found: C, 69.43; H, 4.66; N, 2.31; C₃₃H₂₆NO₅Na.1.5H₂O requires: C, 69.96; H, 5.16; N, 2.47%. ¹H-NMR (CDCl₃): δ = 2.15 (m,2H), 2.50 (t,2H), 2.58 (s,3H), 4.20 (t,2H), 6.91 (d,1H), 7.09 (t,1H), 7.20 (t,1H), 7.28–7.45 (m,10H), 7.55–7.65 (m,4H) ppm. |
| 40 | direct link | (CH₂)₃ | CH₃ | CH₃ | 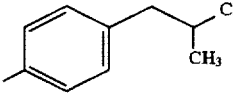 CH₃ / CH₃ | 511 (m+) | Found: C, 74.75; H, 6.66; N, 2.54; C₃₂H₃₃NO₅ requires: C, 75.12; H, 6.50; N, 2.74%. ¹H-NMR (CDCl₃): δ = 0.89 (d,6H), 1.85 (m,1H), 2.01 (s,3H), 2.05 (m,2H), 2.12 (m,2H), 2.45 (d,2H), 2.57 (s,3H), 4.20 (m,2H), 6.77 (s,1H), 7.05 (t,1H), 7.17 (d,2H), 7.20–7.41 (m,5H), 7.50 (d,2H) ppm. |
| 41 | direct link | (CH₂)₃ | H | 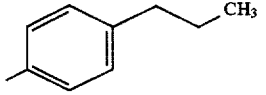 CH₃ | 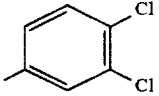 Cl/Cl | 614 (m+) | Found: C, 68.24; H, 4.52; N, 2.22; C₃₅H₂₉NCl₂O₅ requires: C, 68.41; H, 4.76; N, 2.28%. ¹H-NMR (CDCl₃): δ = 1.00 (t,3H), 1.70 (m,2H), 2.27 (m,2H), 2.43 (t,2H), 2.60 (t,2H), 4.30 (t,2H), 6.95 (d,1H), 7.20–7.48 (m,11H), 7.60 (s,1H), 7.78 (s,1H), 8.40 (m,1H) ppm. |
| 42 | direct link | (CH₂)₃ | H | 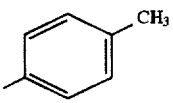 CH₃ | 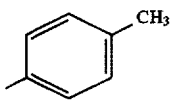 CH₃ | 532 (m+1)⁺ | Found: C, 76.64; H, 5.40; N, 2.48; C₃₄H₂₉NO₅ requires: C, 76.82; H, 5.50; N, 2.63%. ¹H-NMR (CDCl₃): δ = 2.18 (m,2H), 2.35 (s,6H), 2.38 (m,2H), 4.20 (t,2H), 6.90 (d,1H), 7.20 (d,2H), 7.30–7.51 (m,11H), 7.58 (s,1H), 8.40 (m,1H), 9.80 (s,br,1H) ppm. |
| 43 | direct link | (CH₂)₃ | H | H | 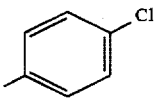 Cl | 462 (m+1)⁺ | Found: C, 66.13; H, 4.13; N, 2.77; C₂₆H₂₀NO₅Cl.1/2H₂O requires: C, 66.32; H, 4.49; N, 2.97%. ¹H-NMR (CDCl₃): δ = 2.20 (m,2H), 2.40 (t,2H), 4.25 (t,2H), 6.90 (d,1H), 7.00 (s,1H), 7.30–7.60 (m,10H), 8.40 (m,1H) ppm. |

-continued

| Ex. No. | X | Y | R | R¹³ | R¹⁴ | m/z | Analysis/$^1$H-NMR/HPLC/Rotation |
|---|---|---|---|---|---|---|---|
| 44 | direct link | (CH$_2$)$_3$ | H | 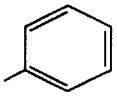 | 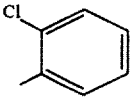 | 538 (m+) | Found: C, 69.19; H, 4.43; N, 2.32; C$_{32}$H$_{24}$NO$_5$Cl.H$_2$O requires: C, 69.13; H, 4.71; N, 2.52%. $^1$H-NMR (CDCl$_3$): δ = 2.23 (m,2H), 2.39 (t,2H), 4.30 (t,2H), 6.98 (d,1H), 7.25– 7.60 (m,14H), 7.90 (m,1H), 8.40 (m,1H) ppm. |
| 45 | direct link | (CH$_2$)$_3$ | H | 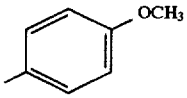 | 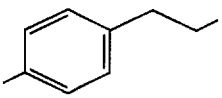 | 575 (m+) | Found: C, 74.91; H, 5.33; N, 2.32; C$_{36}$H$_{33}$NO$_6$ requires: C, 75.11; H, 5.77; N, 2.43%. $^1$H-NMR (CDCl$_3$): δ = 0.95 (t,3H), 1.60 (m,2H), 2.19 (m,2H), 2.38 (t,2H), 2.58 (t,2H), 3.80 (s,3H), 4.24 (t,2H), 6.90 (m,3H), 7.18– 7.50 (m,11H), 7.60 (s,1H), 8.40 (m,1H) ppm. |
| 46 | direct link | (CH$_2$)$_3$ | H | —C≡C—CH$_3$ | 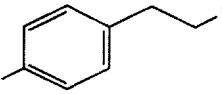 | 507 (m+) | Found: C, 73.98; H, 5.50; N, 2.69; C$_{32}$H$_{29}$O$_5$.0.75H$_2$O requires: C, 73.76; H, 5.61; N, 2.69%. $^1$H-NMR (CDCl$_3$): δ = 0.92 (t,3H), 1.60 (m,2H), 2.01 (s,3H), 2.20 (m,2H), 2.39 (t,2H), 2.58 (t,2H), 4.25 (t,2H), 6.95 (d,1H), 7.20– 7.42 (m,7H), 7.50 (d,2H), 7.58 (s,1H), 8.38 (m,1H) ppm. |
| 47 | direct link | (CH$_2$)$_3$ | H | —(CH$_2$)$_3$OCH$_3$ | 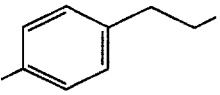 | 542 (m+1)⁺ | $^1$H-NMR (CDCl$_3$): δ = 0.90 (t,3H), 1.60 (m,2H), 1.75 (m,2H), 2.20 (m,2H), 2.38 (m,4H), 2.58 (t,2H), 3.30 (s,3H), 3.40 (m,2H), 4.25 (t,2H), 6.82 (d,1H), 7.20– 7.60 (m,10H), 8.40 (m,1H) ppm. |

Footnotes
$^1$Racemic product from Example 53 used as the starting material.
$^2$Enantiomer B from Example 53 used as the starting material.
$^3$Enantiomer A from Example 53 or the compound of Example 93 used as the starting material.
$^4$Isolated as the sodium salt.

EXAMPLE 48

Ethyl 4-[3-([2,2-diphenyl-1,3-benzodioxolan-5-yl] carbonyl)indol-1-yl]butanoate

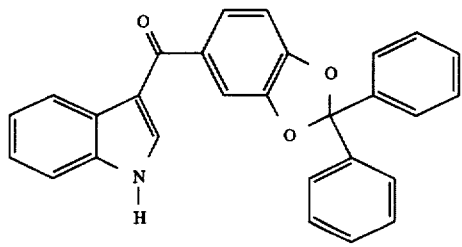

K$_2$CO$_3$, CH$_3$COCH$_2$CH$_3$,
Br(CH$_2$)$_3$CO$_2$C$_2$H$_5$

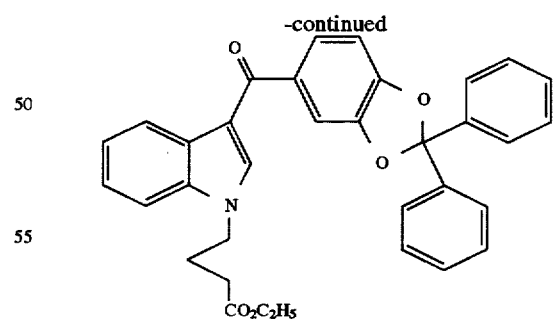

A suspension of 3-[(2,2-diphenyl-1,3-benzodioxolan-5-yl)carbonyl]indole (81.1 g) (see Preparation 4) in 2-butanone was treated with anhydrous potassium carbonate (134 g) and ethyl 4-bromobutyrate (37.9 g). The mixture was mechanically stirred and heated under reflux for 16 hours. After cooling the mixture was filtered and the filtrate evaporated to a golden syrup. Trituration with hexane (3×500 ml)

followed by trituration with diethyl ether (500 ml) gave the title compound as a pink crystalline solid (84.5 g). m.p. 117°–119° C.

Found: C, 77.00; H, 5.43; N, 2.66; $C_{34}H_{29}NO_5$ requires: C, 76.82; H, 5.50; N, 2.63%. m/z=532 (m+1)$^+$ $^1$H-NMR (d$_6$-DMSO): δ=1.05 (t,3H), 2.00 (m,2H), 2.25 (t,2H), 3.90 (q,2H), 4.25 (t,2H), 7.15 (d,1H), 7.25 (m,2H), 7.40–7.60 (m,13H), 8.00 (s,1H), 8.20 (m,1H) ppm.

EXAMPLES 49 to 52

The following compounds of the general formula:

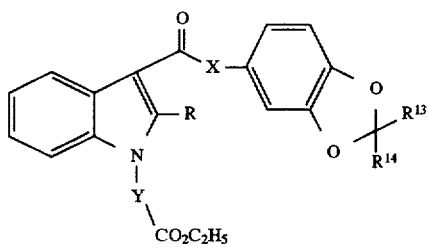

were prepared by alkylation of the appropriate 1H-indole (see Preparations 4, 6 and 10) with the appropriate ethyl bromoalkanoate by similar methods to that used in Example 48.

EXAMPLE 53

Ethyl 4-[3-([2-methyl-2-(4-[2-methylpropyl]phenyl)-1,3-benzodioxolan-5-yl]carbonyl)indol-1-yl]butanoate

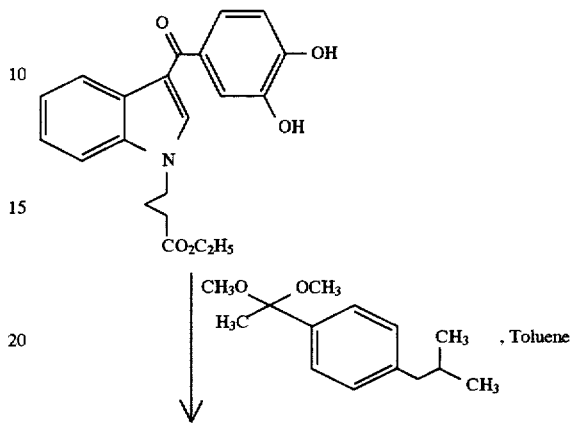

| Ex. No. | X | Y | R | R$^{13}$ | R$^{14}$ | m/z | Analysis/$^1$H-NMR/HPLC |
|---|---|---|---|---|---|---|---|
| 49 | direct link | (CH$_2$)$_2$ | H | phenyl | phenyl | — | Not characterised. |
| 50 | direct link | (CH$_2$)$_4$ | H | phenyl | phenyl | — | Found: C, 77.09; H, 5.88; N, 2.65; C$_{35}$H$_{31}$NO$_5$ requires: C, 77.04; H, 5.72; N, 2.57%. $^1$H-NMR (CDCl$_3$): δ = 1.20 (t,3H), 1.60–1.68 (m,2H), 1.85–2.00 (m,2H), 2.30 (t,2H), 4.10 (q,2H), 4.20 (t,2H), 6.95 (d,1H), 7.27–7.45 (m,10H), 7.58–7.65 (m,6H), 8.40 (m,1H) ppm. |
| 51 | CH$_2$ | (CH$_2$)$_3$ | H | phenyl | phenyl | — | Found: C, 77.26; H, 5.83; N, 2.51; C$_{33}$H$_{31}$NO$_5$ requires: C, 77.04; H, 5.73; N, 2.57%. $^1$H-NMR (CDCl$_3$): δ = 1.25 (t,3H), 2.20 (m,2H), 2.30 (t,2H), 4.05 (s,2H), 4.15 (q,2H), 4.25 (t,2H), 6.75–6.85 (m,2H), 6.90 (s,1H), 7.30–7.40 (m,9H), 7.55–7.60 (m,4H), 7.80 (s,1H), 8.45 (m,1H) ppm. |
| 52 | direct link | (CH$_2$)$_3$ | CH$_3$ | phenyl | phenyl | 546 (m+1)$^+$ | $^1$H-NMR (CDCl$_3$): δ = 1.25 (t,3H), 2.15 (m,2H), 2.40 (t,2H), 2.58 (s,3H), 4.10 (q,2H), 4.20 (t,2H), 6.90 (d,1H), 7.09 (t,1H), 7.20 (t,1H), 7.28–7.45 (m,10H), 7.55–7.65 (m,4H) ppm. |

-continued

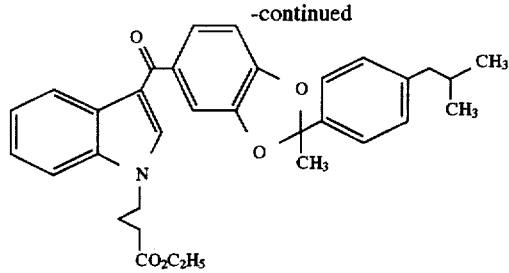

A mixture of 4-isobutylacetophenone dimethyl ketal (3.89 g) (see Preparation 9) and ethyl 4-[3-(3,4-dihydroxybenzoyl)indol-1-yl]butanoate (3.3 g) (see Preparation 5) was suspended in toluene (100 ml) and heated under reflux for one hour in a Dean-Stark apparatus. The first few millilitres of toluene collected in the Dean-Stark trap were removed, the reaction cooled to 60° C. and p-toluenesulphonic acid (50 mg) added to the reaction mixture. The mixture was heated under reflux for 6 hours, cooled and triethylamine (1 ml) added. The mixture was partitioned between diethyl ether (150 ml) and water (150 ml), and the organic layer separated and washed with 2N aqueous sodium hydroxide (100 ml), brine (100 ml) and dried ($MgSO_4$). Evaporation of the organic layer gave a pale brown oil which was subjected to flash chromatography (silica, eluant=3:1 hexane/ethyl acetate) to give the title compound as a pale yellow oil (4.50 g).

Found: C, 75.70; H, 6.69; N, 2.71; $C_{33}H_{35}NO_5$ requires: C, 75.40; H, 6.71; N, 2.66%.

m/z=526 (m+1)$^+$.

$^1$H-NMR (CDCl$_3$): δ=0.90 (d,6H), 1.20 (t,3H), 1.90 (m,1H), 2.05 (s,3H), 2.20 (m,2H), 2.30 (t,2H), 2.45 (d,2H), 4.15 (q,2H), 4.23 (t,2H), 6.85 (d,1H), 7.20 (d,2H), 7.30–7.45 (m,5H), 7.50 (d,2H), 7.60 (s,1H), 8.40 (m,1H ppm.

The above racemic product (514 mg) was resolved into the component enantiomers by passage through a Chiralpak AD (Trade Mark) semi-preparative HPLC column eluting with 85:15 hexane/ethanol at a flow rate of 12 ml/min. The product was resolved batchwise using portions of 40 mg of product in 3 ml eluant (x 10) and 38 mg of product in 3 ml eluant (x 3).

The initially eluted fractions from each batch were combined and concentrated in vacuo to give 231 mg of a single enantiomer A:

Analytical HPLC (Chiralpak AD, Trade Mark), eluant= 85:15 hexane/ethanol at a flow rate of 1 ml/min, RT=17.06 min. (93%).

$[α]_D^{25}$ −98.8° (c=1.0, $CH_2Cl_2$).

Found: C, 75.50; H, 6.97; N, 2.87; $C_{33}H_{35}NO_5$ requires: C, 75.40; H, 6.71; N, 2.66%.

m/z=526 (m+1)$^+$.

$^1$H-NMR (CDCl$_3$): identical to that for above racemate.

The later eluted fractions from each batch were combined and concentrated in vacuo to give 233 mg of a single enantiomer B:

Analytical HPLC (Chiralpak AD, Trade Mark), eluant 85:15 hexane/ethanol at a flow rate of 1 ml/min, RT=22.69 min. (98%).

$[α]_D^{25}$ +101.6° (c=1.0, $CH_2Cl_2$).

Found: C, 75.43; H, 6.92; N, 2.81; $C_{33}H_{35}NO_5$ requires: C, 75.40; H, 6.71; N, 2.66%.

m/z=526 (m+1)$^+$.

$^1$H-NMR (CDCl$_3$): identical to that for above racemate.

EXAMPLES 54 to 92

The following compounds of the general formula:

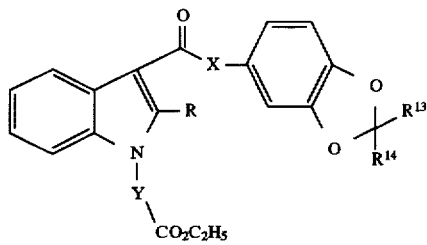

were prepared by reaction of the appropriate catechol derivative (see Preparations 5, 8 and 11) with the appropriate dimethyl ketal or dimethyl acetal (prepared from the corresponding aldehyde or ketone using a similar method to that of Preparation 9) by similar methods to that used in Example 53.

| Ex. No. | X | Y | R | R$^{13}$ | R$^{14}$ | m/z | Analysis/$^1$H−NMR/HPLC |
|---|---|---|---|---|---|---|---|
| 54 | direct link | (CH$_2$)$_3$ | H | 4-(CH$_2$CH(CH$_3$)$_2$)C$_6$H$_4$– | 4-(CH$_2$CH(CH$_3$)$_2$)C$_6$H$_4$– | 616 (m+1)$^+$ | $^1$H-NMR (CDCl$_3$): δ = 0.95 (t,6H), 1.20 (t,3H), 1.65 (m,4H), 2.20 (m,2H), 2.30 (t,2H), 2.59 (m,4H), 4.11 (q,2H), 4.25 (t,2H), 6.95 (d,1H), 7.20 (d,4H), 7.30–7.40 (m,4H), 7.50 (d,4H), 7.61 (s,1H), 7.79 (d,1H), 8.40 (m,1H) ppm. |
| 55 | direct link | (CH$_2$)$_3$ | H | 4-Cl-C$_6$H$_4$– | 4-Cl-C$_6$H$_4$– | 600 (m+) | $^1$H-NMR (CDCl$_3$): δ = 1.20 (t,3H), 2.20 (m,2H), 2.30 (t,2H), 4.10 (q,2H), 4.25 (t,2H), 6.95, (d,1H),7.30–741 (m,9H), 7.50 (s,1H), 7.55 (d,4H), 8.40 (m,1H) ppm. |

| Ex. No. | X | Y | R | R¹³ | R¹⁴ | m/z | Analysis/¹H—NMR/HPLC |
|---|---|---|---|---|---|---|---|
| 56 | direct link | (CH₂)₃ | H | 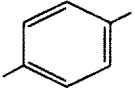 4-F-C₆H₄- | 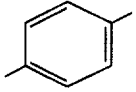 4-F-C₆H₄- | 567 (m+) | ¹H-NMR (CDCl₃): δ = 1.20 (t,3H), 2.20 (m,2H), 2.31 (t,2H), 4.10 (q,2H), 4.25 (t,2H), 6.95 (d,1H), 7.05–7.10 (m,4H), 7.30–7.45 (m,6H), 7.50–7.60 (m,4H), 8.40 (m,1H) ppm. |
| 57 | direct link | (CH₂)₃ | H | —(CH₂)₃CH₃ | 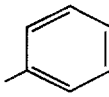 | 554 (m+1)⁺ | ¹H-NMR (CDCl₃): δ = 0.85 (t,3H), 0.90 (t,3H), 1.20 (t,3H), 1.30–1.55 (m,4H), 1.58–1.70 (m,2H), 2.15–2.33 (m,6H), 2.60 (m,2H), 4.10 (q,2H), 4.25 (t,2H), 6.85 (d,1H), 7.20 (d,2H), 7.30–7.42 (m,5H), 7.50 (d,2H), 7.60 (s,1H), 8.40 (m,1H) ppm. |
| 58 | direct link | (CH₂)₃ | H | CH₃ | 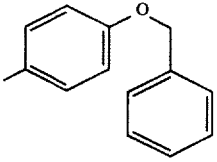 | 576 (m+1)⁺ | ¹H-NMR (CDCl₃): δ = 1.20 (t,3H), 2.05 (s,3H), 2.20 (m,2H), 2.30 (t,2H), 4.10 (q,2H), 4.25 (t,2H), 5.10 (s,2H), 6.85 (d,1H), 7.00 (d,2H), 7.30–7.40 (m,10H), 7.50 (d,2H), 7.55 (s,1H), 8.40 (m,1H) ppm. |
| 59 | direct link | (CH₂)₃ | H | 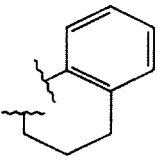 | | 496 (m+1)⁺ | ¹H-NMR (CDCl₃): δ = 1.20 (t,3H), 2.05–2.40 (m,8H), 2.90 (t,2H), 4.10 (q,2H), 4.24 (t,2H), 6.85 (d,1H), 7.20–7.50 (m,8H), 7.58 (d,1H), 7.62 (s,1H), 8.40 (m,1H) ppm. |
| 60 | direct link | (CH₂)₃ | H | 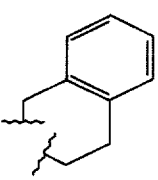 | | 497 (m+1)⁺ | ¹H-NMR (CDCl₃): δ = 1.20 (t,3H), 2.20 (m,2H), 2.25–2.40 (m,4H), 3.15 (t,2H), 3.38 (s,2H), 4.10 (q,2H), 4.25 (t,2H), 6.85 (d,1H), 7.10–7.45 (m,9H), 7.60 (s,1H), 8.40 (m,1H) ppm. |
| 61 | direct link | (CH₂)₃ | H | 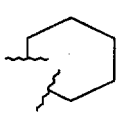 | | 448 (m+1)⁺ | ¹H-NMR (CDCl₃): δ = 1.30 (t,3H), 1.45–1.60 (m,2H), 1.70–1.80 (m,4H), 1.90–2.00 (m,4H), 2.20 (m,2H), 2.34 (t,2H), 4.10 (q,2H), 4.25 (t,2H), 6.80 (d,1H), 7.25–7.40 (m,5H), 7.60 (s,1H), 8.40 (m,1H) ppm. |
| 62 | direct link | (CH₂)₃ | H | 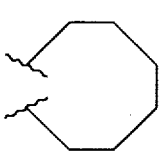 | | 462 (m+1)⁺ | ¹H-NMR (CDCl₃): δ = 1.20 (t,3H), 1.70 (s,br,8H), 2.17 (s,br,6H), 2.35 (t,2H), 4.10 (q,2H), 4.25 (t,2H), 6.80 (d,1H), 7.25–7.45 (m,5H), 7.60 (s,1H), 8.40 (m,1H) ppm. |
| 63 | direct link | (CH₂)₃ | H | CH₃ | 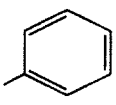 | 469.5 (m+) | ¹H-NMR (CDCl₃): δ = 1.20 (t,3H), 2.05 (s,3H), 2.20 (m,2H), 2.30 (t,2H), 4.10 (q,2H), 4.25 (t,2H), 6.85 (d,1H), 7.30–7.45 (m,8H), 7.59 (s,1H), 7.62 (d,2H), 8.40 (m,1H) ppm. |
| 64 | direct link | (CH₂)₃ | H | 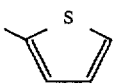 | 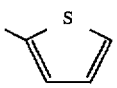 | 544 (m+1)⁺ | ¹H-NMR (CDCl₃): δ = 1.20 (t,3H), 2.20 (m,2H), 2.30 (t,2H), 4.10 (q,2H), 4.25 (t,2H), 6.95–7.05 (m,4H), 7.25–7.50 (m,8H), 7.60 (s,1H), 8.40 (m,1H) ppm. |

-continued

| Ex. No. | X | Y | R | R13 | R14 | m/z | Analysis/1H—NMR/HPLC |
|---|---|---|---|---|---|---|---|
| 65 | direct link | (CH2)3 | H | 2-furyl | 2-furyl | 512 (m+1)+ | 1H-NMR (CDCl3): δ = 1.20 (t,3H), 2.20 (m,2H), 2.30 (t,2H), 4.10 (q,2H), 4.25 (t,2H), 6.45 (m,1H), 6.65 (m,1H), 6.95–7.00 (m,1H), 7.30–7.60 (m,10H), 8.40 (m,1H) ppm. |
| 66 | direct link | (CH2)3 | H | 1-cyano-1-phenyl-cyclohexyl | | 549 (m+1)+ | Found: C, 74.30; H, 5.81; N, 5.10; C34H32N2O5 requires: C, 74.43; H, 5.88; N, 5.11%. 1H-NMR (CDCl3): δ = 1.20 (t,3H), 2.10–2.40 (m,12H), 4.10 (q,2H), 4.20 (t,2H), 6.80 (dd,1H), 7.25–7.60 (m,11H), 8.40 (m,1H) ppm. |
| 67 | direct link | (CH2)3 | H | —(CH2)2CH3 | —(CH2)2CH3 | — | Found: C, 72.26; H, 7.19; N, 2.95; C28H33NO5 requires: C, 72.54; H, 7.18; N, 3.02%. 1H-NMR (CDCl3): δ = 0.90 (t,6H), 1.20 (t,3H), 1.40–1.50 (m,4H), 1.80–1.91 (m,4H), 2.10 (m,2H), 2.45 (t,2H), 4.05 (q,2H), 4.20 (t,2H), 6.70 (d,1H), 7.25–7.40 (m,5H), 7.55 (s,1H), 8.30 (m,1H) ppm. |
| 68 | direct link | (CH2)3 | H | CH3 | cyclohexyl | 476 (m+1)+ | 1H-NMR (CDCl3): δ = 1.10–1.20 (m,8H), 1.55 (s,3H), 1.60–1.90 (m,5H), 2.15 (m,2H), 2.25 (t,2H), 4.10 (q,2H), 4.20 (t,2H), 6.75 (d,1H), 7.20–7.40 (m,5H), 7.55 (s,1H), 8.35 (m,1H) ppm. |
| 69 | direct link | (CH2)3 | H | CH3 | 4-(trifluoromethyl)phenyl | 538 (m+1)+ | 1H-NMR (CDCl3): δ = 1.20 (t,3H), 2.04 (s,3H), 2.20 (m,2H), 2.35 (t,2H), 4.10 (q,2H), 4.25 (t,2H), 6.85 (d,1H), 7.30–7.40 (m,5H), 7.55 (s,1H), 7.70 (d,2H), 7.78 (d,2H), 8.40 (m,1H) ppm. |
| 70 | direct link | (CH2)3 | H | 4-methylphenyl | 2-(4-methylphenyl)ethyl | 588 (m+1)+ | 1H-NMR (CDCl3): δ = 0.95 (t,3H), 1.20 (t,3H), 1.60–1.70 (m,2H), 2.20 (m,2H), 2.28 (t,2H), 2.35 (s,3H), 2.60 (dd,2H), 4.10 (q,2H), 4.25 (t,2H), 6.90 (d,1H), 7.20 (d,4H), 7.25–7.42 (m,5H), 7.45 (d,4H), 7.57 (s,1H), 8.37 (m,1H) ppm. |
| 71 | direct link | (CH2)3 | H | 4-methylbenzyl | 2-(4-methylphenyl)ethyl | 601 (m+) | 1H-NMR (CDCl3): δ = 0.95 (t,3H), 1.18–1.30 (m,6H), 1.55–1.65 (m,2H), 2.20 (m,2H), 2.30 (t,2H), 2.55–2.70 (m,4H), 4.10 (q,2H), 4.25 (t,2H), 6.95 (d,1H), 7.15–7.60 (m,14H), 8.40 (m,1H) ppm. |
| 72 | direct link | (CH2)3 | H | phenyl | 2-(4-methylphenyl)ethyl | 574 (m+1)+ | 1H-NMR (CDCl3): δ = 0.95 (t,3H), 1.20 (t,3H), 1.60–1.70 (m,2H), 2.20 (m,2H), 2.30 (t,2H), 2.60 (dd,2H), 4.10 (q,2H), 4.25 (t,2H), 6.95 (d,1H), 7.20–7.60 (m,15H), 8.40 (m,1H) ppm. |

-continued

| Ex. No. | X | Y | R | R¹³ | R¹⁴ | m/z | Analysis/¹H—NMR/HPLC |
|---|---|---|---|---|---|---|---|
| 73 | direct link | (CH₂)₃ | H | 4-Cl-C₆H₄- | 4-(CH₃)-C₆H₄-CH₂CH₂- | — | Found: C, 73.08; H, 5.47; N, 2.15; C₃₇H₃₄NO₅Cl requires: C, 73.08; H, 5.04; N, 2.30%. ¹H-NMR (CDCl₃): δ = 0.95 (t,3H), 1.20 (t,3H), 1.60–1.70 (m,2H), 2.20 (m,2H), 2.30 (t,2H), 2.60 (dd,2H), 4.10 (q,2H), 4.25 (t,2H), 6.95 (d,1H), 7.20–7.60 (m,14H), 8.40 (m,1H) ppm. |
| 74 | direct link | (CH₂)₃ | H | CH₃ | —C(CH₃)₃ | 450 (m+1)⁺ | ¹H-NMR (CDCl₃): δ = 1.10 (s,9H), 1.20 (t,3H), 1.60 (s,3H), 2.20 (m,2H), 2.30 (t,2H), 4.10 (q,2H), 4.25 (t,2H), 6.80 (d,1H), 7.25–7.45 (m,5H), 7.60 (s,1H), 8.40 (m,1H) ppm. |
| 75 | direct link | (CH₂)₃ | H | —CH₂CH₃ | 4-(CH₃)-C₆H₄-CH₂CH₂- | 526 (m+1)⁺ | ¹H-NMR (CDCl₃): δ = 0.95 (t,3H), 1.05 (t,3H), 1.20 (t,3H), 1.55–1.65 (m,2H), 2.20 (m,2H), 2.30 (m,4H), 2.60 (t,2H), 4.10 (q,2H), 4.25 (t,2H), 6.85 (d,1H), 7.20–7.50 (m,9H), 7.55 (s,1H), 8.40 (m,1H) ppm. |
| 76 | direct link | (CH₂)₃ | H | CH₃ | 4-Cl-C₆H₄- | — | Found: C, 69.22; H, 5.18; N, 2.54; C₂₉H₂₆NO₅Cl requires: C, 69.11; H, 5.20; N, 2.77%. ¹H-NMR (CDCl₃): δ = 1.20 (t,3H), 2.05 (s,3H), 2.20 (m,2H), 2.30 (t,2H), 4.10 (q,2H), 4.25 (t,2H), 6.85 (d,1H), 7.25–7.45 (m,7H), 7.60 (d,2H), 7.62 (s,1H), 8.40 (m,1H) ppm. |
| 77 | direct link | (CH₂)₃ | H | CH₃ | 4-(OCH₃)-C₆H₄- | — | ¹H-NMR (CDCl₃): δ = 1.20 (t,3H), 2.05(s,3H), 2.20 (m,2H), 2.30 (t,2H), 3.80 (s,3H), 4.10 (q,2H), 4.25 (t,2H), 6.85 (d,1H), 6.90 (d,2H), 7.30–7.40 (m,5H), 6.55 (s,1H), 6.60 (d,2H), 8.40 (m,1H) ppm. |
| 78 | direct link | (CH₂)₃ | H | H | 4-(CH₃)-C₆H₄-CH₂CH₂- | 497 (m+) | ¹H-NMR (CDCl₃): δ = 0.95 (t,3H), 1.20 (t,3H), 1.50 (t,2H), 2.10–2.25 (m,2H), 2.30 (t,2H), 2.62 (t,2H), 4.10 (q,2H), 4.25 (t,2H), 6.90 (d,1H), 7.05 (s,1H), 7.30–7.50 (m,9H), 7.60 (s,1H), 8.40 (m,1H) ppm. |
| 79 | direct link | (CH₂)₃ | H | | cyclobutyl-phenyl | 510 (m+1)⁺ | ¹H-NMR (CDCl₃): δ = 1.20 (t,3H), 1.90–2.10 (m,1H), 2.20–2.38 (m,7H), 2.40–2.46 (m,1H), 2.61–2.72 (m,1H), 3.38–4.50 (m,1H), 4.10 (q,2H), 4.25 (t,2H), 6.92 (d,1H), 7.20–7.45 (m,10H), 7.60 (s,1H), 8.40 (m,1H) ppm. |

-continued

| Ex. No. | X | Y | R | R¹³ | R¹⁴ | m/z | Analysis/¹H—NMR/HPLC |
|---|---|---|---|---|---|---|---|
| 80 | direct link | (CH₂)₃ | H | 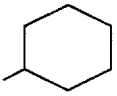 | 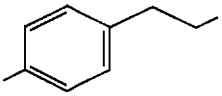 | 579 (m+) | ¹H-NMR (CDCl₃): δ = 0.95 (t,3H), 1.10–1.32 (m,7H), 1.60–1.70 (m,2H), 1.71–1.92 (m,2H), 2.10–2.22 (m,3H), 2.30 (t,2H), 2.60 (t,2H), 4.10 (q,2H), 4.22 (t,2H), 6.80 (d,1H), 7.21 (d,2H), 7.30–7.45 (m,7H), 7.55 (s,1H), 8.40 (m,1H) ppm. |
| 81 | CH₂ | (CH₂)₃ | H | CH₃ | 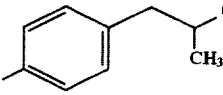 | 541 (m+1)⁺ | ¹H-NMR (CDCl₃): δ = 0.90 (d,6H), 1.30 (t,3H), 1.70–1.95 (m,1H), 2.00 (s,3H), 2.15–2.25 (m,2H), 2.35 (t,2H), 2.50 (d,2H), 4.05 (s,2H), 4.15 (q,2H), 4.25 (t,2H), 6.75 (m,2H), 6.85 (s,1H), 7.15 (d,2H), 7.30–7.42 (m,3H), 7.50 (d,2H), 7.80 (s,1H), 8.45 (m,1H) ppm. |
| 82 | CH₂ | (CH₂)₃ | H | 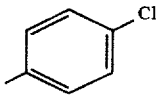 | 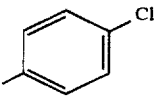 | 615 (m+1)⁺ | ¹H-NMR (CDCl₃): δ = 1.25 (t,3H), 2.10–2.25 (m,2H), 2.30 (t,2H), 4.02 (s,2H), 4.10 (q,2H), 4.23 (t,2H), 6.80 (m,2H), 6.85 (s,1H), 7.25–7.40 (m,9H), 7.45 (d,4H), 7.80 (s,1H), 8.40 (m,1H) ppm. |
| 83 | direct link | (CH₂)₃ | H | CH₃ | 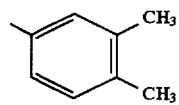 | — | Not characterised. |
| 84 | direct link | (CH₂)₃ | H | CH₃ | 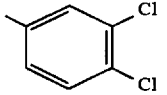 | — | Not characterised. |
| 85 | direct link | (CH₂)₃ | CH₃ | CH₃ | 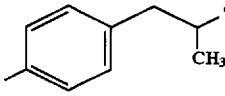 | — | ¹H-NMR (CDCl₃): δ = 0.90 (d,6H), 1.25 (t,3H), 1.85 (m,1H), 2.01 (s,3H), 2.10 (m,2H), 2.40 (m,2H), 2.51 (d,2H), 2.57 (s,3H), 4.15 (q,2H), 4.20 (m,2H), 6.80 (m,1H), 7.05 (t,1H), 7.17 (d,2H), 7.20–7.40 (m,5H), 7.50 (d,2H) ppm. |
| 86 | direct link | (CH₂)₃ | H | 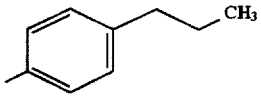 | 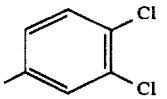 | 642 (m+) | ¹H-NMR (CDCl₃): δ = 0.90 (t,3H), 1.09 (t,3H), 1.60 (m,2H), 2.17 (m,2H), 2.24 (t,2H), 2.58 (t,2H), 4.05 (q,2H), 4.20 (t,2H), 6.95 (d,1H), 7.20–7.50 (m,11H), 7.60 (s,1H), 7.70 (s,1H), 8.35 (m,1H) ppm. |
| 87 | direct link | (CH₂)₃ | H | 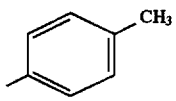 | 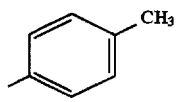 | 560 (m+1)⁺ | Found: C, 77.14; H, 5.47; N, 2.31; C₃₆H₃₃NO₅ requires: C, 77.26; H, 5.94; N, 2.50%. ¹H-NMR (CDCl₃): δ = 1.18 (t,3H), 2.17 (m,2H), 2.30 (t,2H), 2.35 (s,6H), 4.10 (q,2H), 4.20 (t,2H), 6.90 (d,1H), 7.20 (d,4H), 7.25–7.39 (m,5H), 7.45 (d,4H), 7.54 (s,1H), 8.40 (m,1H) ppm. |

| Ex. No. | X | Y | R | R¹³ | R¹⁴ | m/z | Analysis/$^1$H—NMR/HPLC |
|---|---|---|---|---|---|---|---|
| 88 | direct link | (CH$_2$)$_3$ | H | H | 4-chlorophenyl | 489 (m+) | $^1$H-NMR (CDCl$_3$): δ = 1.20 (t,3H), 2.21 (m,2H), 2.40 (t,2H), 4.05 (q,2H), 4.20 (t,2H), 6.90 (d,1H), 7.00 (s,1H), 7.30–7.58 (m,10H), 8.40 (m,1H) ppm. |
| 89 | direct link | (CH$_2$)$_3$ | H | phenyl | 2-chlorophenyl | 566 (m+) | $^1$H-NMR (CDCl$_3$): δ = 1.20 (t,3H), 2.20 (m,2H), 2.31 (t,2H), 4.10 (q,2H), 4.26 (t,2H), 7.00 (d,1H), 7.30–7.60 (m,14H), 7.90 (m,1H), 8.40 (m,1H) ppm. |
| 90 | direct link | (CH$_2$)$_3$ | H | 4-methoxyphenyl | 4-methylphenethyl (CH$_3$) | 603 (m+) | $^1$H-NMR (CDCl$_3$): δ = 0.95 (t,3H), 1.20 (t,3H), 1.60 (m,2H), 2.19 (m,2H), 2.30 (t,2H), 2.60 (t,2H), 3.80 (s,3H), 4.10 (q,2H), 4.24 (t,2H), 6.90 (m,3H), 7.20–7.55 (m,11H), 7.58 (s,1H), 8.40 (m,1H) ppm. |
| 91 | direct link | (CH$_2$)$_3$ | H | —C≡C—CH$_3$ | 4-methylphenethyl (CH$_3$) | 534 (m−1)$^+$ | $^1$H-NMR (CDCl$_3$): δ = 0.92 (t,3H), 1.20 (t,3H), 1.60 (m,2H), 2.04 (s,3H), 2.20 (m,2H), 2.39 (t,2H), 2.58 (t,2H), 4.10 (q,2H), 4.25 (t,2H), 6.85 (d,1H), 7.20–7.45 (m,7H), 7.50 (d,2H), 7.58 (s,1H), 8.38 (m,1H) ppm. |
| 92 | direct link | (CH$_2$)$_3$ | H | —(CH$_2$)$_3$OCH$_3$ | 4-methylphenethyl (CH$_3$) | 570 (m+1)$^+$ | $^1$H-NMR (CDCl$_3$): δ = 0.90 (t,3H), 1.20 (t,3H), 1.60 (m,2H), 1.75 (m,2H), 2.20 (m,2H), 2.38 (m,4H), 2.58 (t,2H), 3.30 (s,3H), 3.40 (t,2H), 4.10 (q,2H), 4.20 (t,2H), 6.85 (d,1H), 7.20–7.60 (m,10H), 8.40 (m,1H) ppm. |

EXAMPLE 93

(−)-Ethyl 4-[3-([2-methyl-2-(4-[2-methylpropyl]phenyl)-1,3-benzodioxolan-5-yl]carbonyl)indol-1-yl]butanoate

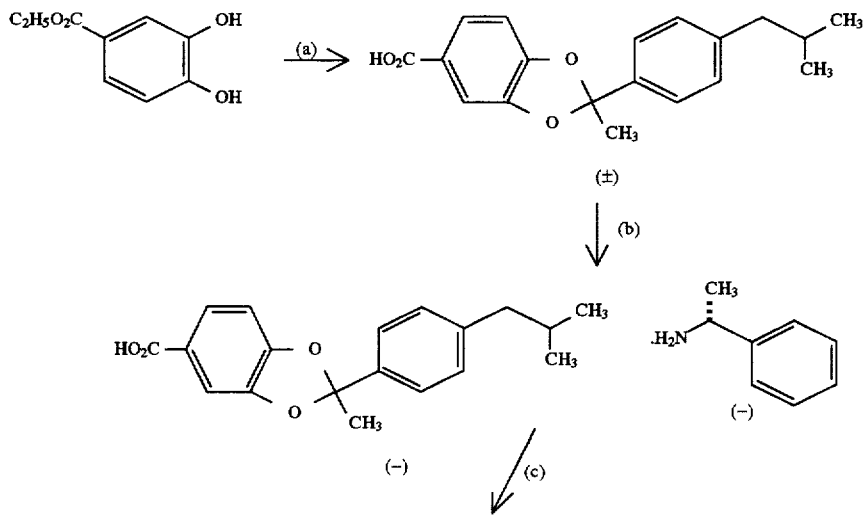

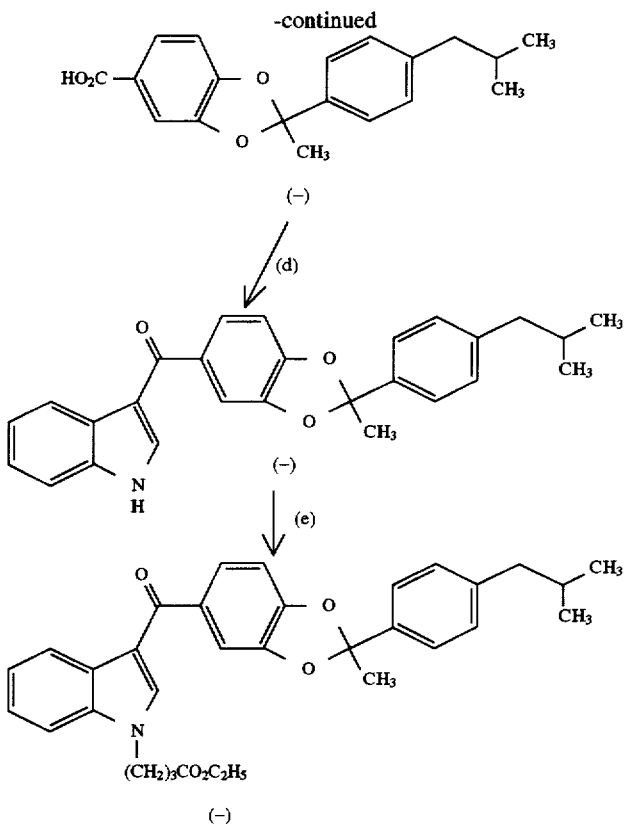

(a) (±)-2-Methyl-2-[4-(2-methylpropyl)phenyl]-1,3-benzodioxolane-5-carboxylic acid A slurry of ethyl 3,4-dihydroxybenzoate (2.51 g) in toluene (20ml) was refluxed for 1 hour in a Dean and Stark apparatus. The ketal of Preparation 9 (2.56 g) was added over 10 minutes and the solution was heated under reflux for 1 hour. The mixture was allowed to cool overnight then p-toluenesulphonic acid (0.065 g) was added and the reaction vessel fitted with a distillation head and condenser. The mixture was heated to 95° C. and formaldehyde dimethyl ketal was distilled off. After heating for 5 hours the mixture was cooled and filtered. The filtrate was diluted with hexane (15 ml) and washed with 10% aqueous sodium bicarbonate (30 ml). The organic layer was evaporated in vacuo to provide a brown oil (3.45 g).

This material was dissolved in aqueous methylated spirit (15 ml) and 2N aqueous sodium hydroxide (7.6 ml) was added. The mixture was heated under reflux for 3 hours, cooled and treated with hexane (12.5 ml) and 2N aqueous hydrochloric acid (9 ml). The organic phase was separated, washed with brine (4 ml) and left to stand. The resulting crystalline precipitate was filtered off and dried to provide the title compound (1.47g), m.p. 156°–158° C.

$^1$H-NMR (CDCl$_3$): δ=0.90 (d,6H) , 1.85 (m,1H), 2.00 (s,3H), 2.48 (d,2H), 6.82 (d,1H), 7.20 (d,2H), 7.45–7.52 (m,3H), 7.70 (d,1H) ppm.

(b) (-)-2-Methyl-2-[4-(2-methylpropyl)phenyl]-1,3-benzodioxolane-5-carboxylic acid, (-)-α-methylbenzylamine salt A solution of the compound of part (a) (1 g) in aqueous acetone (2% water, 6 ml) was treated with L-(-)-α-methylbenzylamine (0.39 g) and the resulting mixture was stirred overnight. The resulting precipitate was filtered off, washed with acetone and dried to give the title compound (0.29 g), m.p. 155°–8° C.

HPLC [Cyclobond I β-SN cyclodextrin column eluting with 30:70 0.05M aqueous triethylammonium acetate (pH4) /acetonitrile at a flow rate of 1 ml/min.]
RT=6.98 min. (99%).

$^1$H-NMR (CDCl$_3$): δ=0.87 (d,6H), 1.47 (d,3H), 1.85 (m,1H), 2.00 (s,3H), 2.48 (d,2H), 4.18 (q,1H), 6.60 (d,1H), 7.00 (s,br,3H), 7.10–7.32 (m,9H), 7.50 (d,2H) ppm.

(c) (-)-2-Methyl-2-[4-(2-methylpropyl)phenyl]-1,3-benzodioxolane-5-carboxylic acid The compound of part (b) (0.29 g) was stirred with 1N aqueous hydrochloric acid (2 ml) overnight and then filtered. The solid material was washed with 1N aqueous hydrochloric acid (1 ml), water (1 ml) and dried to give the title compound (0.21 g), $[α]_D^{25}$ -149.40 (c=1, methanol), m.p. 120°–2° C.

HPLC [Cyclobond I β-SN cyclodextrin column eluting with 30:70 0.05M aqueous triethylammonium acetate (pH4) /acetonitrile at a flow rate of 1 ml/min.]
RT=6.9 min (99%).

$^1$H-NMR (CDCl$_3$)-Identical to that obtained for the product of part (a).

(d) (-)-3-([2-Methyl-2-(4-[2-methylpropyl]phenyl)-1,3-benzodioxolan-5-yl]carbonyl)indole The compound of part (c) (3.12 g) was dissolved in toluene (15 ml) and treated with pyridine (0.9 g). This mixture was slowly added to a solution of thionyl chloride (1.2 g) in toluene (15 ml). After stirring for one hour the mixture was filtered and the filtrate evaporated to provide the acid chloride as an oil which was used directly in the next stage.

A solution of indole (2.5 g) in toluene (15 ml) was rapidly added to a solution of methylmagnesium iodide (7.3 ml of a 3M solution in diethyl ether) in toluene (30 ml). The mixture was cooled to –60° C., stirred for 20 minutes and was then treated with a solution of the acid chloride prepared above in toluene (5 ml) over 3 minutes. The mixture was stirred at −35° C. for 1 hour and then was quenched with saturated aqueous ammonium chloride (50 ml). The mixture was warmed to room temperature and ethyl acetate added (100 ml). The organic layer was separated and evaporated in vacuo to give the title compound as a white solid (3.2 g), m.p. 155°–8° C., $[a]_D^{25}$ −166.1° (c=1, methanol).

HPLC [Cyclobond I β-SN cyclodextrin column eluting with 75:25 methanol/water at a flow rate of 1.2 ml/min.] RT=19 min. (98.2%).

$^1$H-NMR (CDCl$_3$): δ=0.85 (d,6H), 1.85 (m,1H), 2.00 (s,3H), 2.50 (d,2H), 6.82 (d,1H), 7.20 (d,2H), 7.22–7.40 (m,5H), 7.50 (d,2H), 7.60 (d,1H), 8.40 (m,1H), 9.10 (s,br, 1H) ppm.

(e) (-)-Ethyl 4-[3-([2-methyl-2-(4-[2-methylpropyl]-phenyl) -1,3-benzodioxolan-5-yl]carbonyl)indol-1-yl]butanoate A mixture of the compound of part (d) (2.88 g), potassium carbonate (3.9 g), ethyl 4-bromobutyrate (1.7 g) and 2-butanone (25 ml) was heated under reflux for 5 hours. The mixture was cooled, filtered and the filtrate evaporated to give a viscous gum which was purified by flash chromatography (silica, 9:1 hexane/ethyl acetate) to provide the title compound as a clear gum (3.2 g).

This compound was analytically and spectroscopically identical to Enantiomer A of Example 53.

The following Preparations illustrate the preparation of certain starting materials used in the previous Examples:

PREPARATION 1

2,2-Diphenyl-1,3-benzodioxolane-5-carboxylic acid, ethyl ester

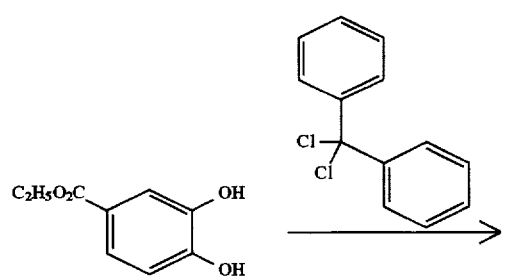

A mixture of ethyl 3,4-dihydroxybenzoate (20 g) and dichlorodiphenylmethane (22.9 ml) was heated in an oil bath at 170° C. for 10 minutes during which time HCl gas was given off. The reaction mixture was cooled to give the title compound as a buff coloured solid (38.0 g).

PREPARATION 2

2,2-Diphenyl-1,3-benzodioxolane-5-carboxylic acid

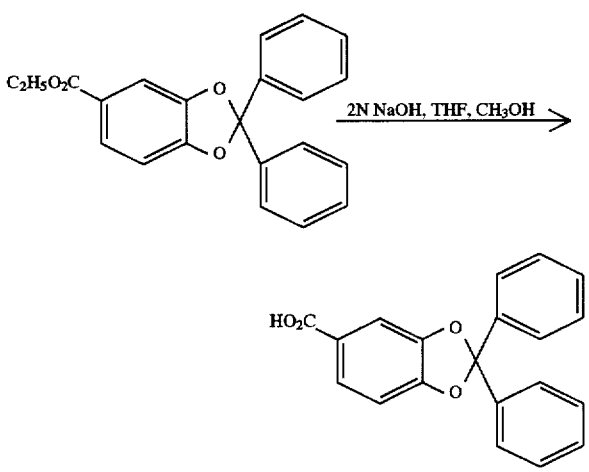

A solution of the compound of Preparation 1 (38 g) in THF (239 ml) and methanol (239 ml) was treated with 2N aqueous sodium hydroxide (460 ml). After stirring at 40° C. for 6 hours the reaction mixture was concentrated in vacuo and acidified with 2N aqueous hydrochloric acid. The resultant buff coloured precipitate was collected and dried to give the title compound (34.5 g), m.p. 213° C., m/z=318(m+).

$^1$H-NMR (d$_6$-DMSO) δ=6.90 (d,1H), 7.30–7.55 (m,12H) ppm.

PREPARATION 3

2,2-Diphenyl-1,3-benzodioxolane-5-carbonyl chloride

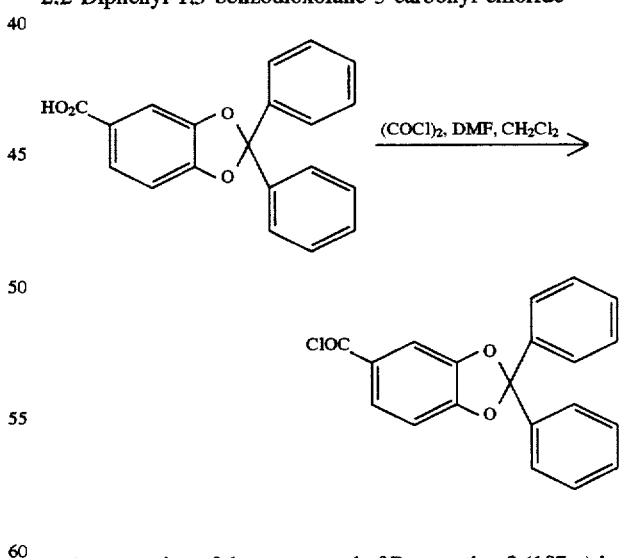

A suspension of the compound of Preparation 2 (107 g) in dichloromethane (500 ml) was cooled to 0° C. and treated with oxalyl chloride (44 ml) and dimethylformamide (DMF) (5 drops). After stirring for 1½ hours the clear solution was evaporated and azeotroped three times with dichloromethane to give the title compound as a brown crystalline solid (112 g).

PREPARATION 4

3-[(2,2-Diphenyl-1,3-benzodioxolan-5-yl) carbonyl]indole

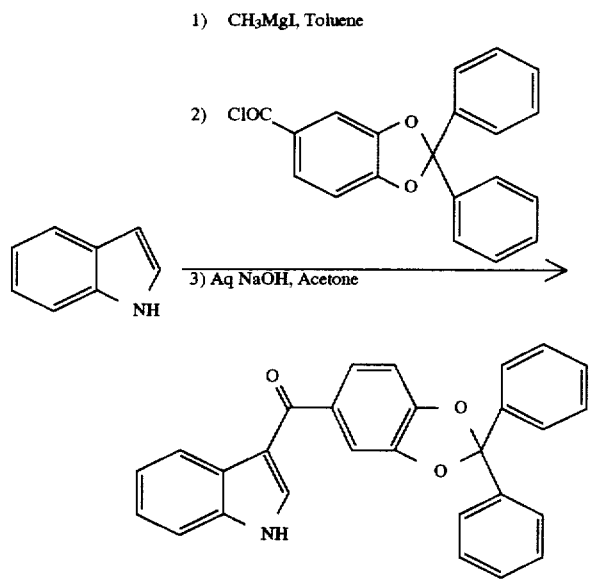

A mechanically stirred solution of indole (35.7 g) in toluene (250 ml) was cooled to 0° C. and treated with methylmagnesium iodide (112 ml of a 3.0M solution in diethyl ether). After stirring at room temperature for 30 minutes a solution of the compound of Preparation 3 (11 g) in toluene (500 ml) was added dropwise with rapid stirring. Stirring was continued at room temperature for 2 hours then 10% aqueous ammonium chloride solution (500 ml) was added and the aqueous phase extracted with ethyl acetate (1.5 L). The organic layer was separated and evaporated in vacuo to give a buff solid. The crude solid was suspended in acetone (500 ml) and treated with a solution of sodium hydroxide (15 g) in water (100 ml). The mixture was heated under reflux for 3 hours and then poured onto ice. The resultant beige precipitate was collected and dried to give the title compound (103.9 g). m/z =418 (m+1)$^+$.

$^1$H-NMR (d$_6$-DMSO): δ=7.15 (d,1H), 7.20 (m,1H), 7.40–7.60 (m,14H), 7.95 (s,1H), 8.20 (m,1H) ppm.

PREPARATION 5

Ethyl 4-[3-(3,4-dihydroxybenzoyl)indol-1-yl]butanoate

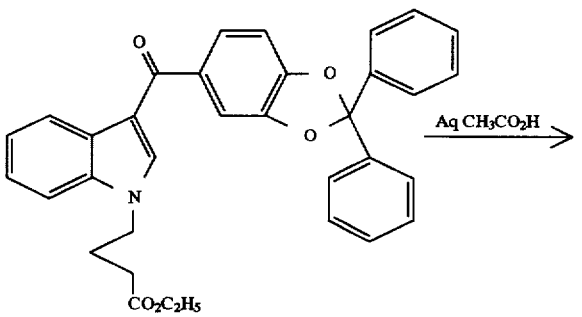

The compound of Example 48 (100 mg) was dissolved in acetic acid/water (9:1) (2 ml) and heated under reflux for 2 hours. The reaction mixture was cooled, evaporated in vacuo to dryness and the residue partitioned between ethyl acetate and brine. The organic layer was separated, dried (MgSO$_4$) and evaporated in vacuo to a brown oil. Flash chromatography (silica, initially eluting with 3:7 ethyl acetate/hexane and finally with ethyl acetate using the gradient elution technique) gave the title compound as a pale brown foam (54 mg). m/z=367 (m+).

$^1$H-NMR (d$_6$-DMSO): δ=1.05 (t,3H), 2.00 (m,2H), 2.25 (t,2H), 3.25 (s.br,2H), 3.95 (q,2H), 4.25 (t,2H), 6.80 (d,1H), 7.15–7.25 (m,4H), 7.60 (d,1H), 7.95 (s,1H), 8.20 (d,1H) ppm.

PREPARATION 6

3-[(2,2-Diphenyl-1,3-benzodioxolan-5-yl) methylcarbonyl] indole

The title compound was prepared by a similar method to that of Preparation 4 using indole and (2,2-diphenyl-1,3-benzodioxolan-5-yl)acetyl chloride (prepared from the corresponding carboxylic acid [see Preparation 7] by a similar method to that of Preparation 3) as the starting materials.

m/z =431 (m+).

$^1$H-NMR (d$_6$-DMSO): δ=4.00 (s, 2H), 6.80 (d,1H), 6.90 (d,1H), 6.95 (s,1H), 7.05–7.10 (m,2H), 7.30–7.50 (m,11H), 8.10 (d,1H), 8.41 (s,1H) ppm.

PREPARATION 7

[2,2-Diphenyl-1,3-benzodioxolan-5-yl]acetic acid

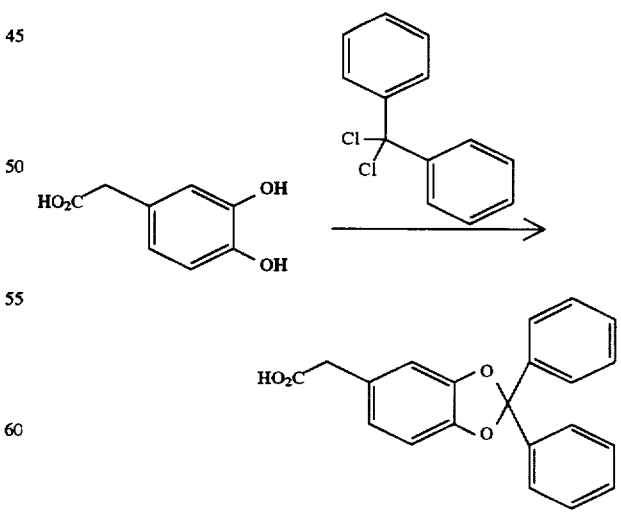

A mixture of 3,4-dihydroxyphenylacetic acid (5.0 g) and dichlorodiphenylmethane (7.05 g) was heated at 150° C. for 20 minutes with stirring. A stream of nitrogen was passed over the reaction mixture to drive off the HCl gas that formed. The mixture was cooled and the residue partitioned between diethyl ether and 2N aqueous sodium hydroxide. The basic layer was separated, acidified (conc. hydrochloric acid) and the resulting solid collected by filtration to give the title compound (5.00 g), m/z =333 (m+1)$^+$.

Found: C, 75.54; H, 5.04; N, 0.0; $C_{21}H_{16}O_4$ requires: C, 75.83; H, 4.85; N, 0.0%.

$^1$H-NMR (d$_6$-DMSO): δ=3.42 (s,2H), 6.70 (d,1H), 6.85–6.90 (m,3H), 7.40–7.55 (m,10H) ppm.

PREPARATION 8
Ethyl 4-[3-(3,4-dihydroxyphenacyl)indol-1-yl]butanoate

The title compound was prepared by a similar method to that of Preparation 5 using the compound of Example 51 as the starting material.

$^1$H-NMR (d$_6$-DMSO): δ=1.15 (t,3H), 2.10 (m,2H), 2.30 (t,2H), 3.90 (s,2H), 4.00 (q,2H), 4.25 (t,2H), 6.55–6.60 (m,2H), 6.70 (s,1H), 7.10–7.30 (m,2H), 7.60 (d,1H), 8.15 (d,1H), 8.50 (s,1H) ppm.

PREPARATION 9
4-Isobutylacetophenone dimethyl ketal

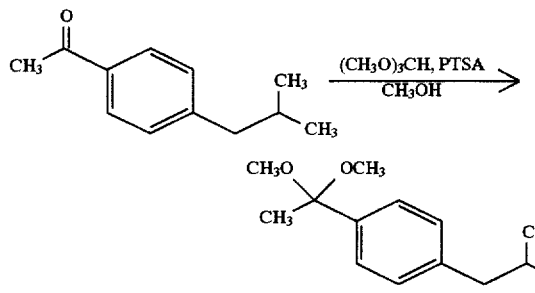

A mixture of 4-isobutylacetophenone (2.9 ml), trimethylorthoformate (5.3 ml), methanol (30 ml) and p-toluenesulphonic acid (PTSA) (50 mg) was gently heated and the methyl formate produced was allowed to distil off through a short vigreux column. The cooled reaction mixture was basified (using a few drops of a 30% w/w solution of sodium methoxide in methanol) and the reaction was partitioned between water (100 ml) and diethyl ether (100 ml). The ether layer was separated, washed with saturated brine solution (100 ml), dried (MgSO$_4$) and evaporated in vacuo to give a colourless oil (3.60 g).

$^1$H-NMR (CDCl$_3$): δ=0.90 (d,6H), 1.55 (s,3H), 1.85 (m,1H), 2.45 (d,2H), 3.20 (s,6H), 7.10 (d,2H), 7.38 (d,2H) ppm.

PREPARATION 10
3-[(2,2-Diphenyl-1,3-benzodioxolan-5-yl)-carbonyl]-2-methylindole The title compound was prepared by a similar procedure to that of Preparation 4 with the exception that 2-methylindole replaced indole as the starting material.
m/z=432 (m+1)$^+$.

$^1$H-NMR (CDCl$_3$): δ=2.58 (s,3H), 6.87 (d,1H), 7.04 (t,1H), 7.15 (t,1H), 7.30–7.48 (m,10H), 7.55–7.64 (m,4H), 8.43 (s,br,1H) ppm.

PREPARATION 11
Ethyl 4-[3-(3,4-dihydroxybenzoyl)-2-methylindole-1-yl] butanoate The title compound was prepared by a similar procedure to that of Preparation 5 using the compound of Example 52 as the starting material.

m/z =382 (m+1)$^+$ $^1$H-NMR (d$_6$-DMSO): δ=1.15 (t,3H), 1.90 (m,2H), 2.38 (s,3H), 2.45 (m,2H), 4.00 (q,2H), 4.20 (m,2H), 6.77 (d,1H), 6.90–7.15 (m,4H), 7.25–7.38 (m,1H), 7.50 (d,1H), 9.40 (s,br,2H) ppm.

Pharmacological activity

A selection of compounds of the formula (I) was tested in vitro for steroid 5α-reductase inhibitory activity using ventral prostate tissue from male rats according to the procedure outlined on pages 35 to 37 of the description. The results are presented in Table 1.

TABLE 1

| Example No. | IC$_{50}$ (nM) |
|---|---|
| 1 | 2.7 |
| 2 | 11.4 |
| 4 | 10.3 |
| 5 | 33.7 |
| 6 | 15.6 |
| 7 | 10.7 |
| 8 | 2.9 |
| 9 | 67.5 |
| 10 | 7.91 |
| 14 | 21.1 |
| 15 | 5.29 |
| 19 | 11.0 |
| 27 | 1.41 |
| 29 | 3.67 |
| 31 | 5.56 |
| 34 | 264 |
| 35 | 42.6 |
| 36 | 251 |
| 37 | 100 |
| 39 | 270 |
| 40 | 260 |
| 45 | 7.84 |

Toxicity Study

The compound of Example 4 was administered orally to mice up to a dose of 1000 mg/kg and the animal showed normal appearance and behaviour throughout the duration of the study.

What is claim is:
1. A compound of the formula:

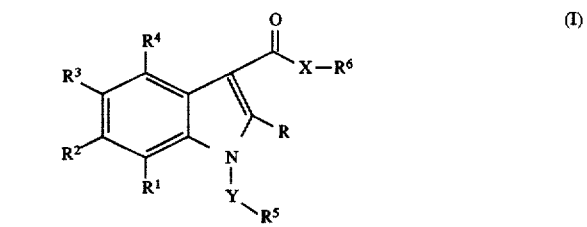

or a pharmaceutically acceptable salt thereof,
wherein

X is O, NH, N(C$_1$–C$_4$ alkyl), direct link, C$_1$–C$_4$ alkylene, C$_2$–C$_4$ alkenylene or C$_2$–C$_4$ alkynylene, said alkylene, alkenylene and alkynylene being optionally substituted by C$_1$–C$_4$ alkyl or aryl;

Y is methylene, C$_2$–C$_6$ alkylene optionally interrupted by O, C$_2$–C$_6$ alkenylene or C$_2$–C$_6$ alkynylene, all of which may be optionally substituted by C$_1$–C$_6$ alkyl, or is a group of the formula:

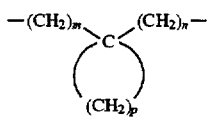

wherein m and n are each independently selected from 0 and an integer of from 1 to 5, with the proviso that the sum of m and n is not greater than 5, and p is an integer of from 2 to 6;

R is H, OH, halo, $C_1$–$C_4$ alkyl or $C_1$–$C_4$ alkoxy;

$R^1$, $R^2$, $R^3$ and $R^4$ are each independently selected from H, $C_1$–$C_4$ alkyl, $C_1$–$C_4$ alkoxy, OH, halo, —$CF_3$, —$CO_2(C_1$–$C_4$ alkyl), —$CONH_2$, —$CONH(C_1$–$C_4$ alkyl) and —$CON(C_1$–$C_4$ alkyl)$_2$;

$R^5$ is —COOH, —$COOR^7$, —$CONR^8R^9$ or tetrazol-5-yl;

$R^6$ is

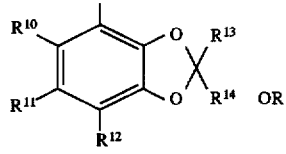  OR

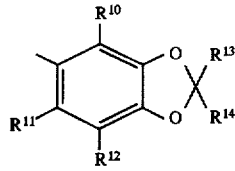

$R^7$ is a biolabile ester-forming group;

$R^8$ and $R^9$ are each independently selected from H and $C_1$–$C_4$ alkyl;

$R^{10}$, $R^{11}$ and $R^{12}$ are each independently selected from H, $C_1$–$C_4$ alkyl, $C_1$–$C_4$ alkoxy, —OH, halo and halo($C_1$–$C_4$ alkyl);

$R^{13}$ and $R^{14}$ are each independently selected from H, $C_1$–$C_{10}$ alkyl, $C_1$–$C_{10}$alkoxy, $C_2$–$C_6$ alkenyl, $C_2$–$C_6$ alkynyl, $C_3$–$C_8$ cycloalkyl, —$CO_2(C_1$–$C_4$ alkyl), —$CONR^8R^9$, —CN, halo($C_1$–$C_6$ alkyl), aryl and heteroaryl, said alkyl and alkoxy groups being optionally substituted by $C_1$–$C_6$ alkoxy, $C_3$–$C_7$ cycloalkyl, —OH, —$CO_2(C_1$–$C_4$ alkyl), –$CONR^8R^9$, –CN, aryl, aryloxy or heteroaryl, and said alkenyl and alkynyl groups being optionally substituted by aryl, with the proviso that $R^{13}$ and $R^{14}$ are not both H, or $R^{13}$ and $R^{14}$, taken together with the carbon atom to which they are attached, represent optionally benzo-fused spiro ($C_3$–$C_8$)cycloalkane, said spirocycloalkane group and the benzo-fused portion being optionally substituted by $C_1$–$C_6$ alkyl, $C_1$–$C_6$ alkoxy, $C_3$–$C_8$ cycloalkyl, —OH, —$CO_2(C_1$–$C_4$ alkyl), —$CONR^8R^9$, —CN, halo($C_1$–$C_6$ alkyl), aryl or heteroaryl, or $R^{13}$ and $R^{14}$, taken together with the carbon atom to which they are attached, represent spiropyrrolidine or spiropiperidine, both of which may be optionally N-substituted by $C_1$–$C_6$ alkyl, $C_2$–$C_6$ alkanoyl, $C_2$–$C_6$ alkanoyl($C_1$–$C_4$ alkyl)- or arylcarbonyl;

"aryl" used in the definitions of X, $R^{13}$ and $R^{14}$ means phenyl optionally substituted by $C_1$–$C_6$ alkyl, $C_1$–$C_6$ alkoxy, $C_2$–$C_6$ alkenyl, OH, halo, halo($C_1$–$C_6$ alkyl), nitro, amino, $C_2$–$C_6$ alkanamido, $C_2$–$C_6$ alkanoyl, —$CO_2(C_1$–$C_4$ alkyl), phenyl, phenyl($C_1$–$C_4$)alkoxy or —$(CH_2)_q CONR^8R^9$ wherein q is 0 or an integer of from 1 to 4;

and "heteroaryl" used in the definitions of $R^{13}$ and $R^{14}$ means a five- or six-membered heteroaromatic group which contains from 1 to 4 heteroatoms each independently selected from N, O and S and which is optionally substituted by $C_1$–$C_4$ alkyl, $C_1$–$C_4$ alkoxy, halo, —OH or halo($C_1$–$C_4$ alkyl).

2. A compound as claimed in claim 1 wherein

X is a direct link or $C_1$–$C_4$ alkylene,

Y is $C_1$–$C_6$ alkylene,

R is H or $C_1$–$C_4$ alkyl, $R^1$, $R^2$, $R^3$ and $R^4$ are each H, $R^5$ is —COOH or —COO($C_1$–$C_6$ alkyl), $R^6$ is

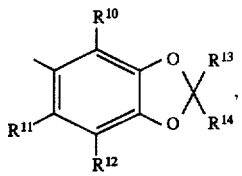

$R^{10}$, $R^{11}$ and $R^{12}$ are as defined in claim 1 and $R^{13}$ and $R^{14}$ are each independently selected from H, $C_1$–$C_{10}$ alkyl optionally substituted by $C_1$–$C_6$ alkoxy, $C_2$–$C_6$ alkynyl, $C_3$–$C_8$ cycloalkyl, phenyl optionally substituted by $C_1$–$C_6$ alkyl, $C_1$–$C_6$ alkoxy, halo, halo($C_1$–$C_6$ alkyl) or phenyl($C_1$–$C_4$)alkoxy, thienyl and furyl, or $R^{13}$ and $R^{14}$, taken together with the carbon atom to which they are attached, represent optionally benzofused spiro ($C_5$–$C_7$)cycloalkane, optionally substituted by —CN or phenyl.

3. A compound as claimed in claim 2 wherein

X is a direct link or methylene,

Y is ethylene, propylene or butylene,

R is H or methyl, $R^5$ is —COOH or —$CO_2C_2H_5$, $R^{10}$, $R^{11}$ and $R^{12}$ are each H and $R^{13}$ and $R^{14}$ are each independently selected from H, methyl, ethyl, n-propyl, n-butyl, t-butyl, 3-methoxyprop-1-yl, 1-propynyl, cyclohexyl, phenyl, 4-methylphenyl, 4-ethylphenyl, 4-(n-propyl)phenyl, 4-(2-methylpropyl)phenyl, 3,4-dimethylphenyl, 4-fluorophenyl, 2-chlorophenyl, 4-chlorophenyl, 3,4-dichlorophenyl, 4-methoxyphenyl, 4-trifluoromethylphenyl, 4-benzyloxyphenyl, cyclohexyl, 2-thienyl and 2-furyl, or $R^{13}$ and $R^{14}$, taken together with the carbon atom to which they are attached, represent spirocyclohexane, spirocycloheptane, or a group of the formula:

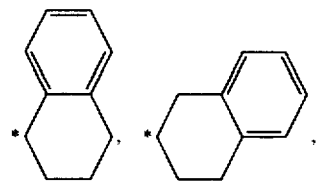

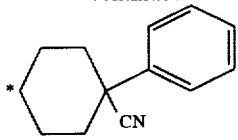 OR

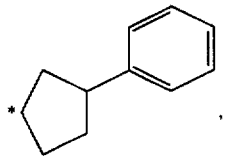

where * represents the spiro carbon atom in common with the 1,3-benzodioxolane ring.

4. A compound as claimed in claim 3 wherein
X is a direct link, Y is propylene, R is H,
$R^5$ is —COOH or —$CO_2C_2H_5$,
$R^{13}$ is methyl and $R^{14}$ is 4-(2-methylpropyl)phenyl.

5. A compound as claimed in claim 1 wherein $R^5$ is —COOH.

6. A compound as claimed in claim 1 which is (-)-4-[3-([2-methyl-2-(4-[2-methylpropyl]phenyl)-1,3-benzodioxolan-5-yl]carbonyl)indol-1-yl]butanoic acid and (-)-ethyl 4-[3-([2-methyl-2-(4-[2-methylpropyl]phenyl)-1,3-benzodioxolan-5-yl]carbonyl)indol-1-yl]butanoate, or a pharmaceutically acceptable salt of either thereof.

7. A compound as claimed in claim 1 wherein the pharmaceutically acceptable salt is the sodium, potassium, N-benzyl-N-(2-phenylethyl)amine or 1-adamantylamine salt.

8. A pharmaceutical composition comprising an amount of a compound according to claim 1 effective in inhibiting steroid 5-alpha reductase, together with a pharmaceutically acceptable diluent or carrier.

9. A method of treatment of a human to inhibit a steroid 5α-reductase which comprises treating said human with an effective amount of a compound of the formula (I) or with a pharmaceutically acceptable salt or composition thereof, as claimed in claim 1.

10. A method of treatment of a human for acne vulgaris, alopecia, seborrhoea, female hirsutism, benign prostatic hypertrophy, male pattern baldness or a human prostate adenocarcinoma which comprises treating said human with an effective amount of a compound of the formula (I) or with a pharmaceutically acceptable salt or composition thereof, as in claim 1.

11. A compound of the formula:

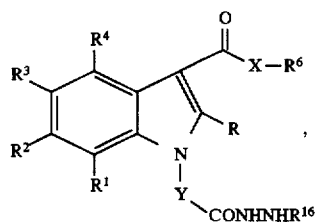 (III)

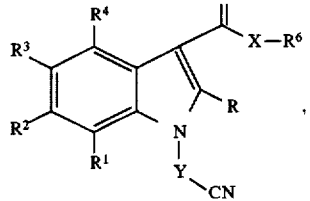 (IV)

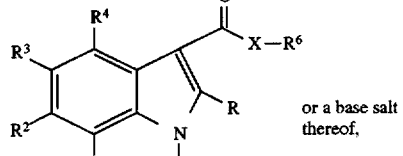 (VIII)

or a base salt thereof,

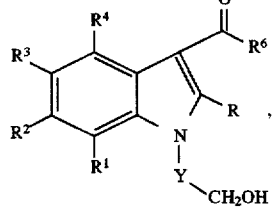 (XVIII)

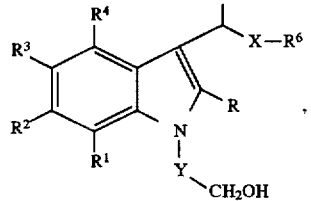 (XIX)

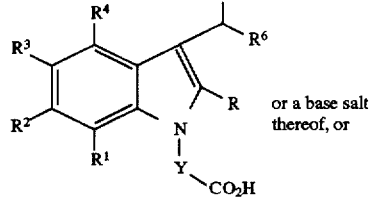 (XX)

or a base salt thereof, or

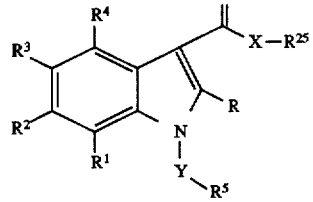 (XXIII)

or, where $R^5$ is —COOH, a base salt thereof, wherein $R^{16}$ is H or $C_1$–$C_4$ alkyl, $R^{24}$ is H or OH.

$R^{25}$ is

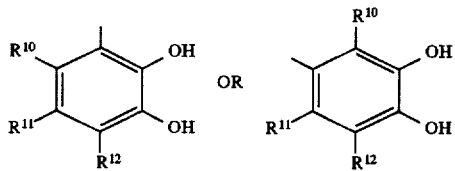

and X, Y, R, $R^1$, $R^2$, $R^3$, $R^4$, $R^5$, $R^6$, $R^{10}$, $R^{11}$ and $R^{12}$ are as defined in claim 1 for a compound of the formula (I).

12. A compound of the formula (VIII) as claimed in claim 11 which is 3-([2-methyl-2-(4-[2-methylpropyl]phenyl)-1,3-benzodioxolan-5-yl]carbonyl)indole or (-)-3-([2-methyl-2-(4-[2-methylpropyl]phenyl)-1,3-benzodioxolan-5-yl]carbonyl)indole, or a base salt of either thereof.

13. 2-Methyl-2-[4-(2-methylpropyl)phenyl]-1,3-benzodioxolane-5-carboxylic acid, or (-)-2-methyl-2-[4-(2-methylpropyl)phenyl]-1,3-benzodioxolane-5-carboxylic acid or the (-)-α-methylbenzylamine salt thereof.

14. A pharmaceutical composition comprising an amount of a compound according to claim 1 effective in inhibiting steroid 5-alpha reductase for treating a condition selected from acne vulgaris, alopecia, seborrhea, female hirsutism, benign prostatic hypertrophy, male pattern baldness, and human prostate adenocarcinoma, together with a pharmaceutically acceptable diluent or carrier.

* * * * *